United States Patent [19]
Zlock et al.

[11] Patent Number: 5,944,739
[45] Date of Patent: Aug. 31, 1999

[54] SUTURE ANCHOR INSTALLATION SYSTEM

[75] Inventors: Stephen W. Zlock, Hawthorne, N.Y.;
Dennis M. Stefura, Trumbull; Peter C. Miller, Bethel, both of Conn.;
Christine M. Tompkins, Washington, D.C.

[73] Assignee: Surgical Dynamics, Inc., Norwalk, Conn.

[21] Appl. No.: 09/041,219

[22] Filed: Mar. 12, 1998

[51] Int. Cl.⁶ .................................................... A61B 17/04
[52] U.S. Cl. .......................... 606/232; 606/139; 606/144; 206/63.3; 206/339
[58] Field of Search ..................................... 606/139, 144, 606/232; 206/63.3, 339

[56] References Cited

U.S. PATENT DOCUMENTS

| | | | |
|---|---|---|---|
| 3,768,635 | 10/1973 | Eggert | 206/380 |
| 3,910,281 | 10/1975 | Kletschka et al. | 606/232 |
| 4,135,623 | 1/1979 | Thyen | 206/63.3 |

(List continued on next page.)

FOREIGN PATENT DOCUMENTS

| | | |
|---|---|---|
| 232049 | 8/1987 | European Pat. Off. . |
| 241240 | 10/1987 | European Pat. Off. . |
| 376641 | 7/1990 | European Pat. Off. . |
| 464479A1 | 1/1992 | European Pat. Off. . |
| 465910A1 | 1/1992 | European Pat. Off. . |
| 2622430 | 5/1989 | France . |
| 4 106823C1 | 6/1992 | Germany . |
| WO92/04874 | 4/1992 | WIPO . |

OTHER PUBLICATIONS

Acufex Microsurgical Inc., "Technique for Using the TAG™ Tissue Anchor—Wedge Style".
Arthrex, "The Complete Arthrex Information System".
Mitek Surgical Products, "Mitek GII Anchor, High Strength Fixation", 1991.
Mitek Surgical Products, "Mitek Anchor System, Effective Soft Tissue Reattachment", 1990.
Mitek Surgical Products, "Mitek Quick Anchor, Fast, Effective, Soft Tissue Reattachment", 1990.
Zimmer, Inc., "STATAK™ Soft Tissue Attachment Device", 1988.
Acufex Microsurgical Inc., "TAG™ Tissue Anchor Guide System".
Acufex Microsurgical Inc., "Technique for Using the TAG™ Tissue Anchor—Rod Style".

*Primary Examiner*—Gary Jackson

[57] ABSTRACT

A suture anchor installation system includes a body portion having a distal end and a proximal end, an elongated shaft extending distally from the distal end of the body portion, the shaft having a distal end with an annular region disposed at the distal end of the shaft. A suture anchor is attachable within the annular region and comprising a setting portion and an engagement portion, the suture anchor having at least one suture associated therewith. A suture retaining member is positioned on the body portion, the suture retaining member including tabs to grip the at least one suture extending from the suture anchor to maintain the setting portion within the engagement portion. A loading unit for use with a suturing apparatus is mountable on the body portion including a mounting member positioned on the body portion and configured to releasably hold at least one suture needle, the at least one suture needle being associated with the at least one suture extending from the suture anchor. The loading unit further includes a receiving structure formed in the body portion for receiving a distal end portion of the suturing apparatus in operative alignment with mounting member to facilitate mounting of the at least one surgical needle in the suturing apparatus. A method for applying a suture anchor comprises the steps of providing a suture anchor installation system, implanting the suture anchor into a bone, securing the suture anchor within the bone, mounting the suture apparatus into the receiving structure of the loading unit, loading the at least one suture needle into the suturing apparatus, and suturing the suture anchor to soft tissue with the at least one suture needle.

36 Claims, 24 Drawing Sheets

U.S. PATENT DOCUMENTS

| | | | |
|---|---|---|---|
| 4,236,470 | 12/1980 | Stenson | 112/169 |
| 4,275,717 | 6/1981 | Bolesky . | |
| 4,424,898 | 1/1984 | Thyen et al. | 206/63.3 |
| 4,520,511 | 6/1985 | Gianezio et al. . | |
| 4,591,048 | 5/1986 | Eldridge, Jr. . | |
| 4,621,640 | 11/1986 | Mulhollan et al. . | |
| 4,632,100 | 12/1986 | Sommers et al. | 606/232 |
| 4,699,271 | 10/1987 | Lincoln et al. . | |
| 4,738,255 | 4/1988 | Goble et al. | 606/232 |
| 4,741,330 | 5/1988 | Hayhurst | 606/232 |
| 4,870,957 | 10/1989 | Goble et al. | 606/232 |
| 4,871,289 | 10/1989 | Choiniere . | |
| 4,898,156 | 2/1990 | Gatturna et al. | 606/232 |
| 4,898,505 | 2/1990 | Froelich . | |
| 4,899,743 | 2/1990 | Nicholson et al. . | |
| 4,921,383 | 5/1990 | Fischer . | |
| 4,927,421 | 5/1990 | Goble et al. | 606/232 |
| 4,946,468 | 8/1990 | Li | 606/232 |
| 4,968,315 | 11/1990 | Gatturna | 606/232 |
| 5,002,550 | 3/1991 | Li . | |
| 5,013,316 | 5/1991 | Goble et al. . | |
| 5,015,250 | 5/1991 | Foster . | |
| 5,037,422 | 8/1991 | Hayhurst . | |
| 5,041,129 | 8/1991 | Hayhurst et al. . | |
| 5,046,513 | 9/1991 | Gatturna et al. . | |
| 5,078,730 | 1/1992 | Li et al. . | |
| 5,080,543 | 1/1992 | Murphy . | |
| 5,084,050 | 1/1992 | Draenert . | |
| 5,085,661 | 2/1992 | Moss . | |
| 5,100,417 | 3/1992 | Cerier et al. . | |
| 5,102,421 | 4/1992 | Anspach, Jr. . | |
| 5,131,533 | 7/1992 | Alpern . | |
| 5,176,682 | 1/1993 | Chow . | |
| 5,207,679 | 5/1993 | Li . | |
| 5,217,486 | 6/1993 | Rice et al. . | |
| 5,258,016 | 11/1993 | DiPoto et al. . | |
| 5,354,298 | 10/1994 | Lee et al. . | |
| 5,389,103 | 2/1995 | Melzer et al. . | |
| 5,441,502 | 8/1995 | Bartlett . | |
| 5,478,344 | 12/1995 | Stone et al. . | |
| 5,478,345 | 12/1995 | Stone et al. . | |
| 5,522,844 | 6/1996 | Johnson . | |
| 5,534,011 | 7/1996 | Greene, Jr. et al. . | |
| 5,569,301 | 10/1996 | Granger et al. . | |
| 5,571,090 | 11/1996 | Sherts . | |
| 5,578,057 | 11/1996 | Wenstrom, Jr. | 606/232 |
| 5,681,352 | 10/1997 | Clancy, III et al. | 606/232 |
| 5,752,963 | 5/1998 | Allard et al. | 606/139 |
| 5,782,862 | 7/1998 | Bonutti | 606/232 |
| 5,814,051 | 9/1998 | Wenstrom, Jr. | 606/104 |
| 5,827,291 | 10/1998 | Fucci et al. | 606/104 |

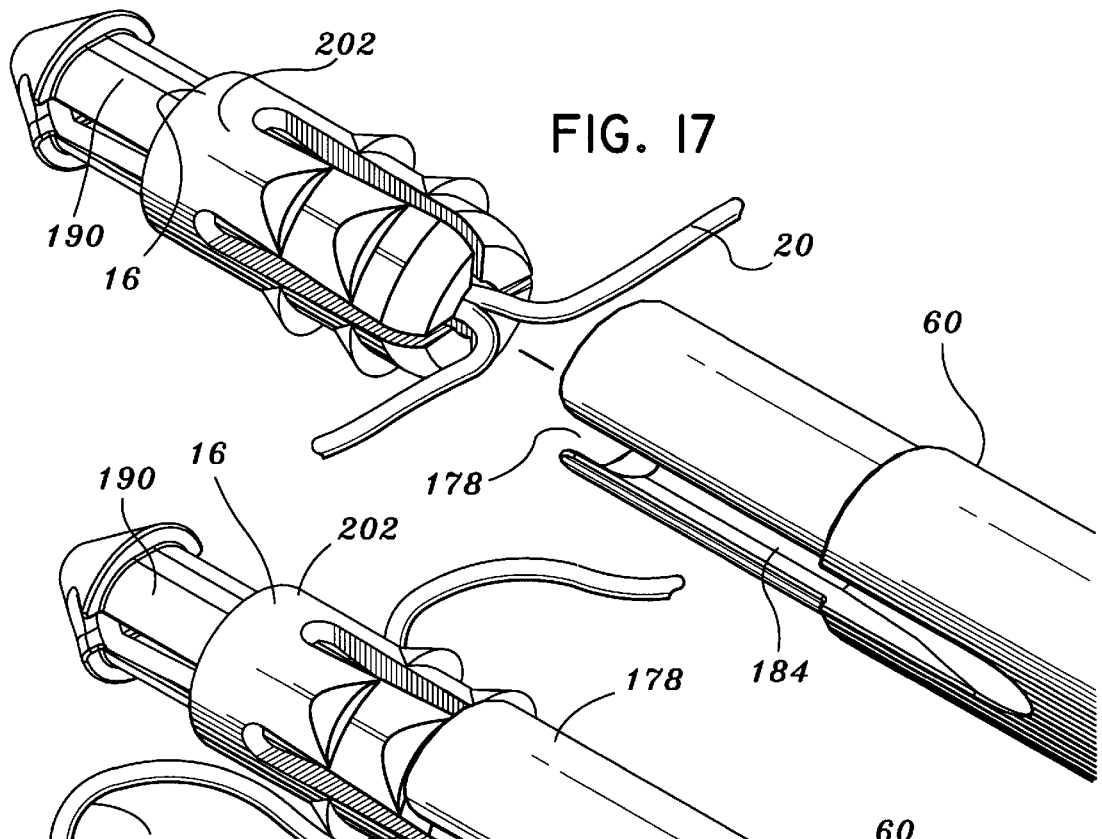
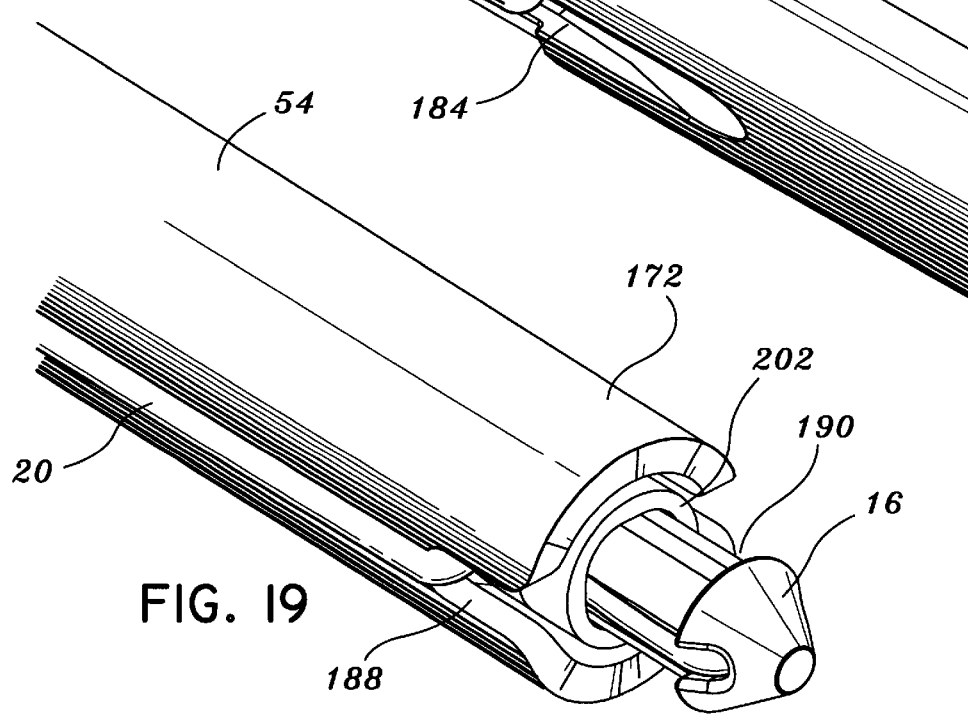

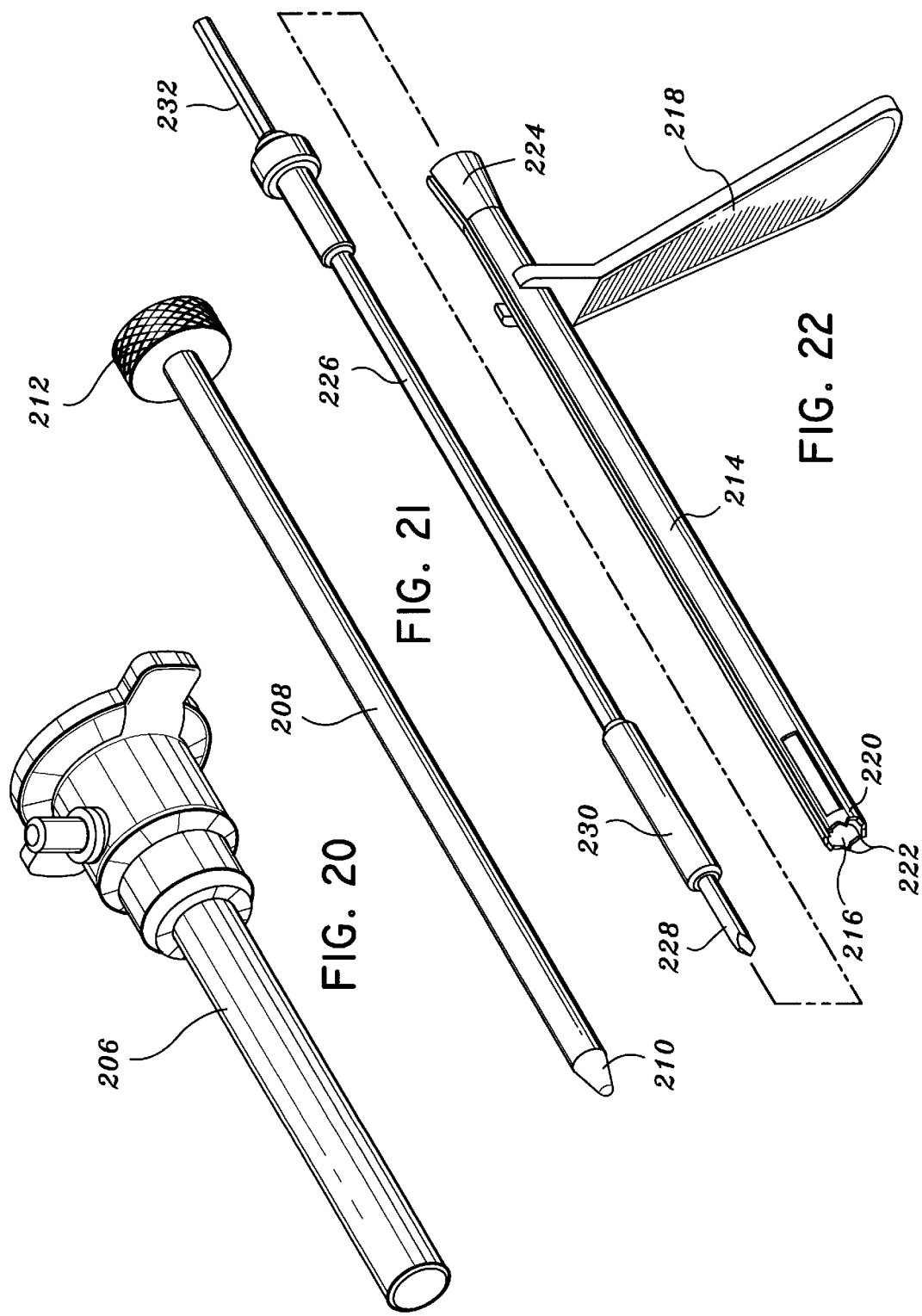

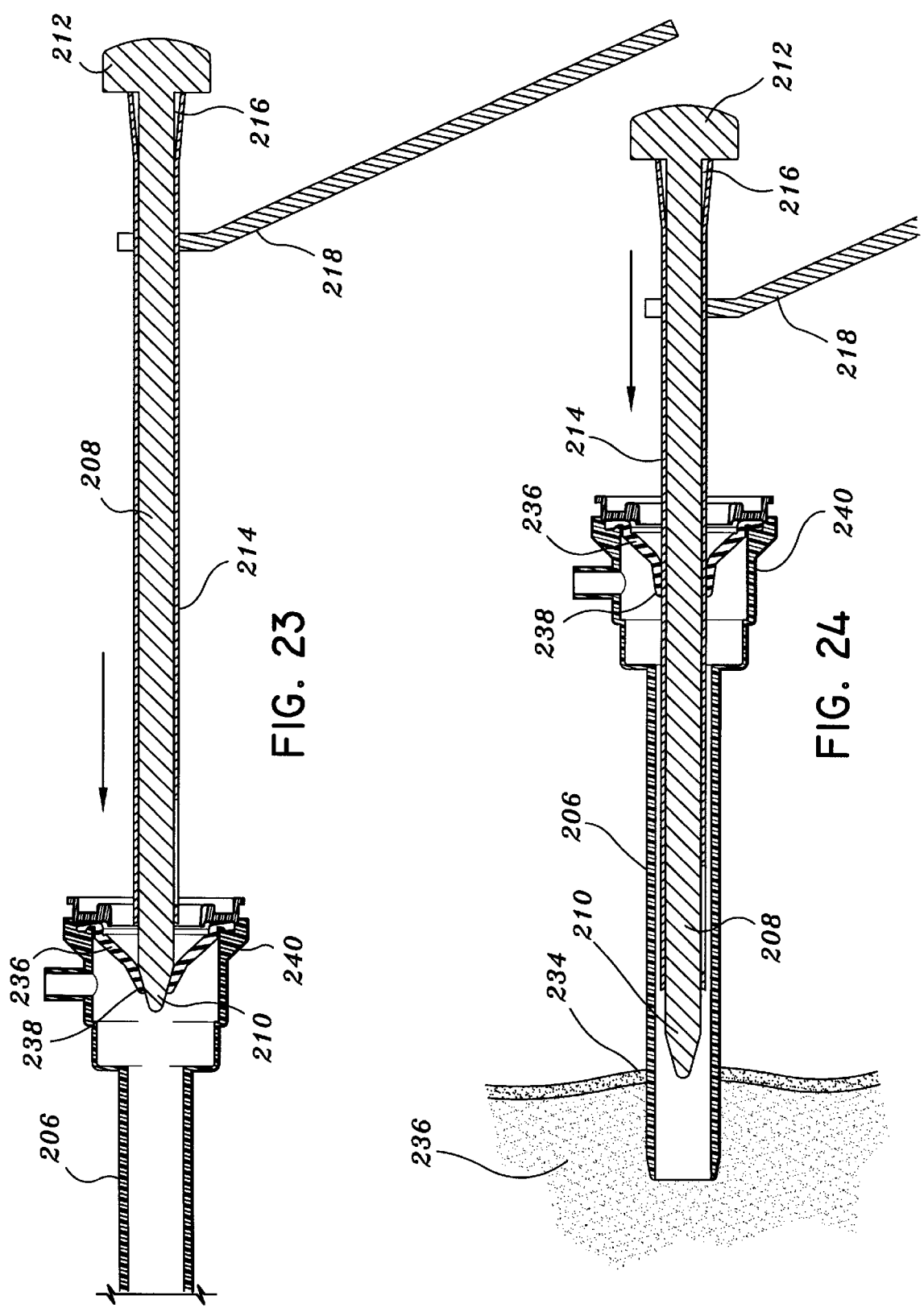

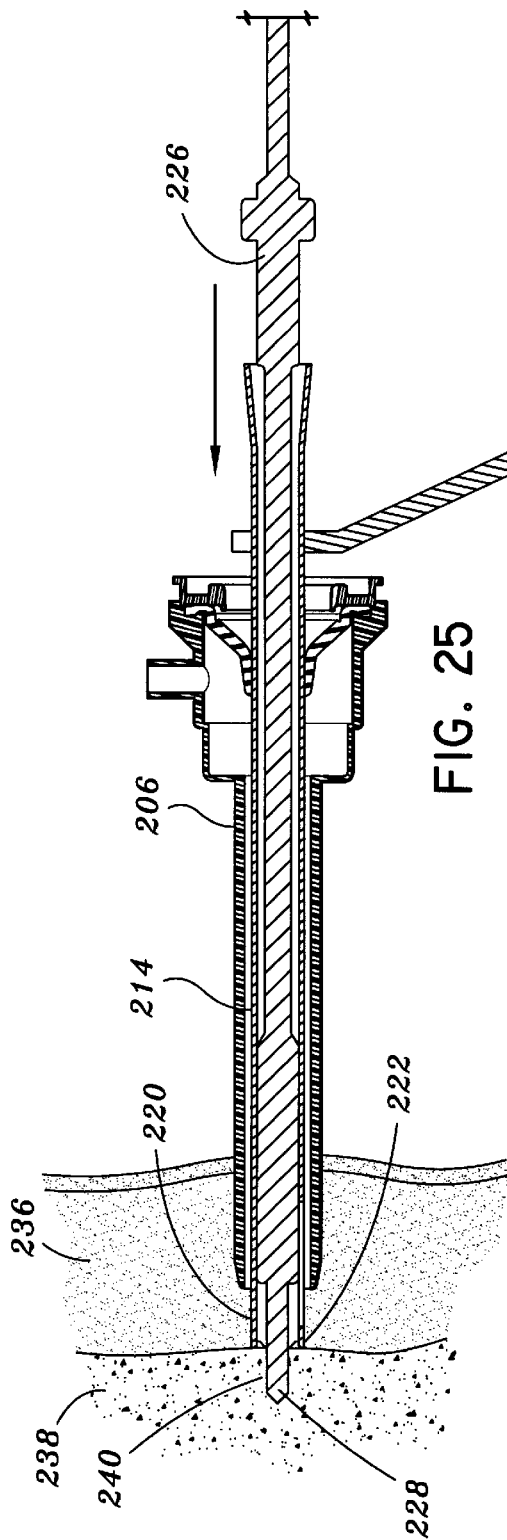
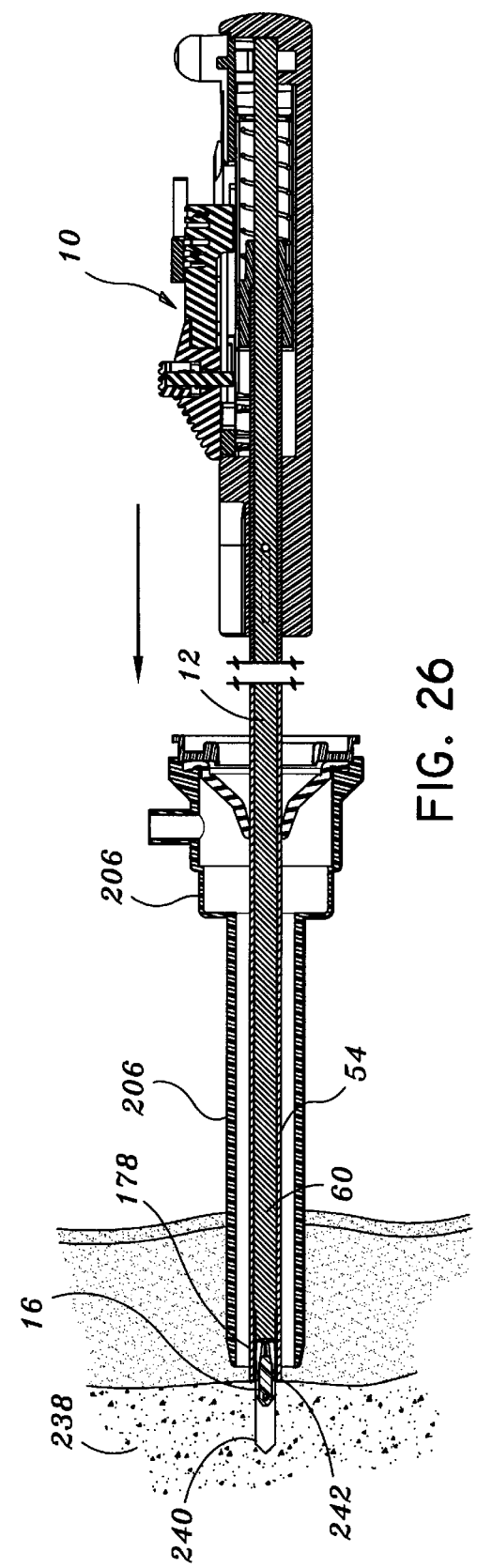

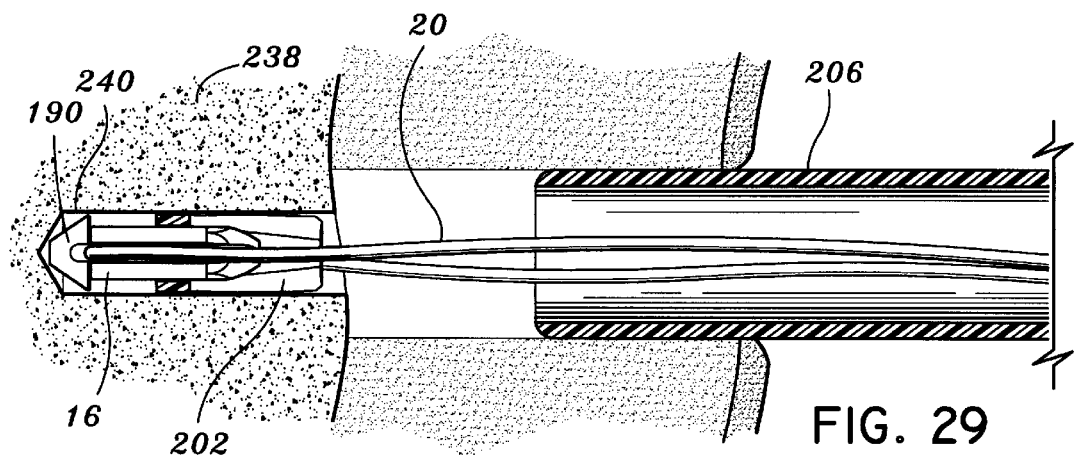
FIG. 29
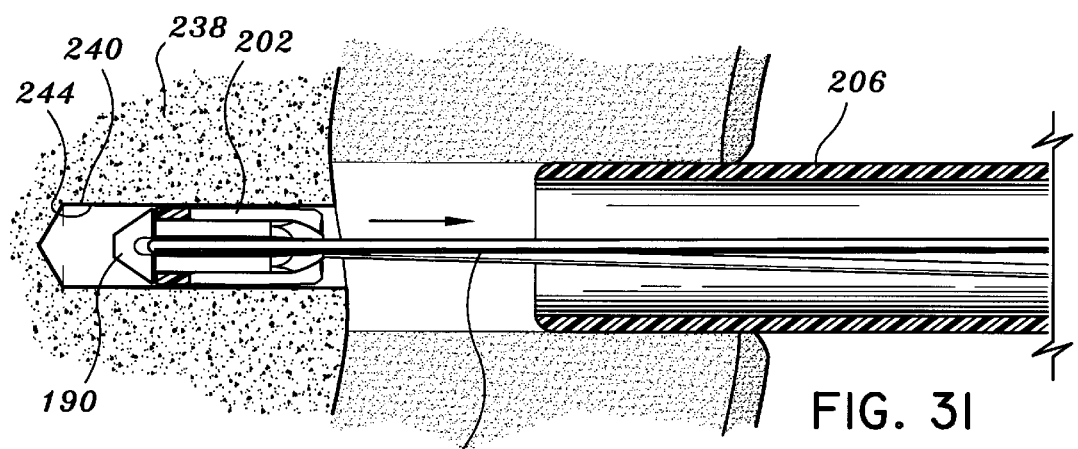
FIG. 31
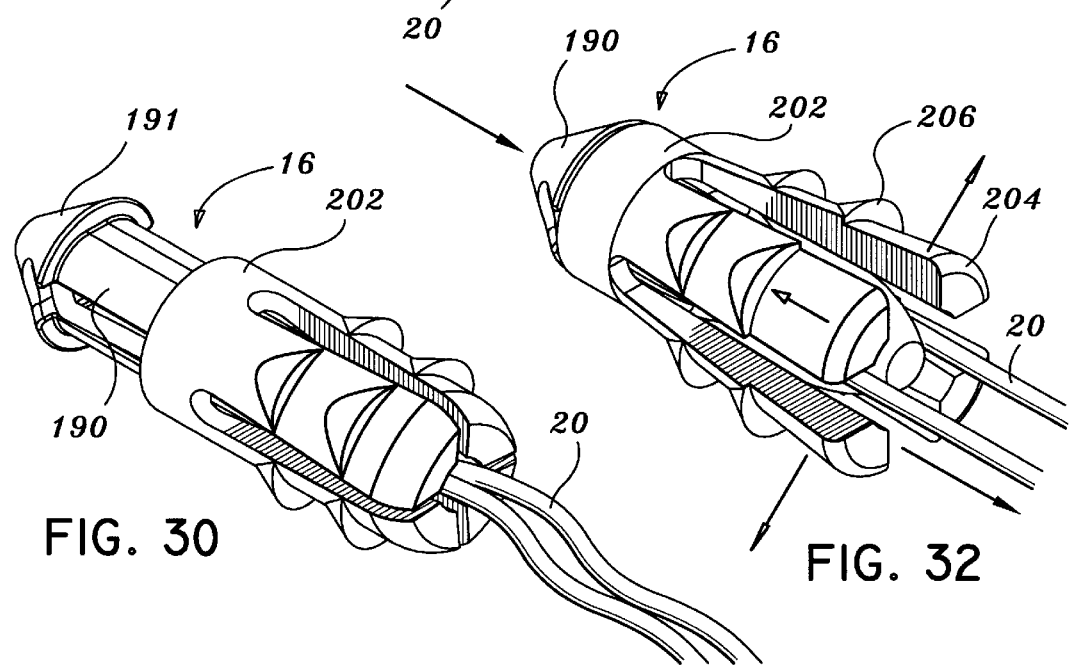
FIG. 30
FIG. 32

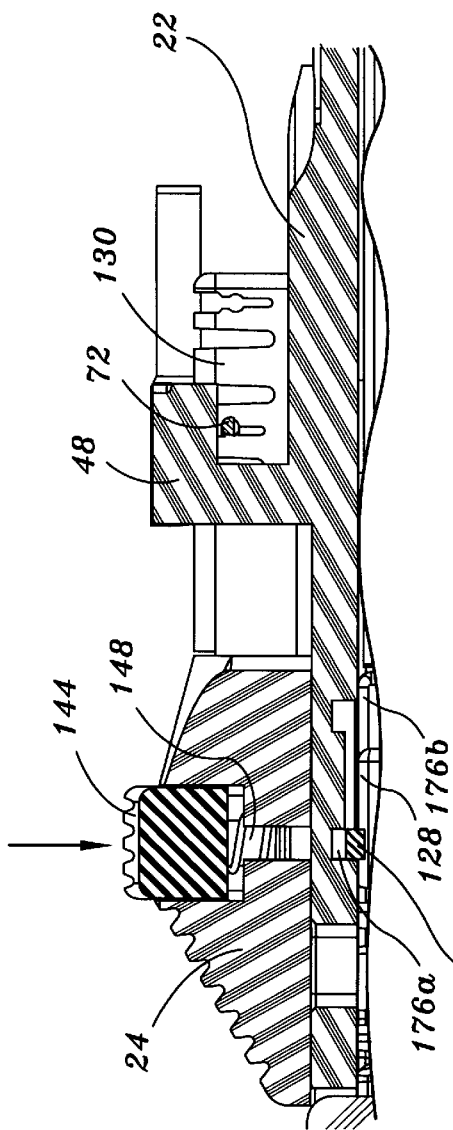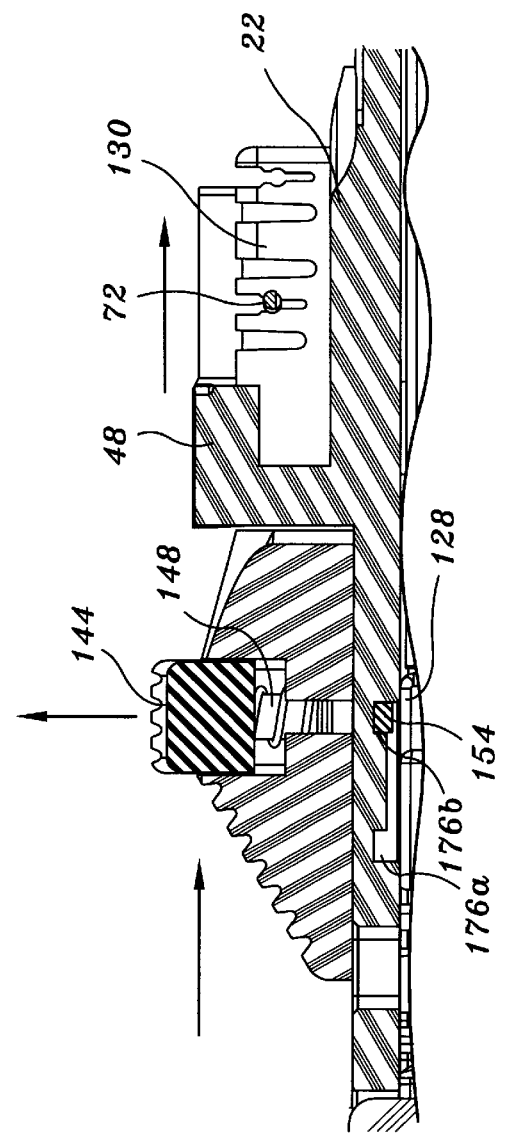

SUTURE ANCHOR INSTALLATION SYSTEM

BACKGROUND

1. Technical Field

This disclosure relates to an apparatus and method for a suture installation system and, more particularly, to a suture anchoring system including a suture anchor insertion tool having a loading unit for a suturing apparatus.

2. Background of Related Art

During surgery, it is often necessary to attach muscle tissue or prosthetic implants to bone. Suture anchors are used to facilitate such attachment by securing a suture to bone. Generally, an anchor is implanted into hole predrilled into a bone mass. A suture engaged by the suture anchor extends from the bone and is used to stitch the muscle tissue or prosthetic device to the bone. Suture anchors find particular use in joint reconstruction surgery, especially during the attachment of ligaments or tendons to bones in the knee, shoulder or elbow.

A suture anchor installation system is disclosed in U.S. Pat. No. 5,354,298 issued to Lee et al. (Lee et al.) and assigned to United States Surgical Corporation and is incorporated herein by reference. The suture anchor installation system is composed of a suture anchor insertion tool mounting a suture anchor assembly. The suture anchor assembly includes a suture anchor which can be easily implanted yet remain firmly lodged within a predrilled hole in bone. Surgical needles are preattached to a suture engaged by the suture anchor. The suture anchor installation system in Lee et al. provides suture needles for suturing soft tissue to bone. The suture needles provided are the type in which the suture is administered by hand by a surgeon.

Suturing soft tissue by hand can be tedious and time consuming. One way of avoiding suturing by hand is to use the suturing apparatus disclosed in U.S. Pat. No. 5,478,344 to Stone et al. (Stone et al.), assigned to United States Surgical Corporation, and incorporated herein by reference. The suturing apparatus described in Stone et al. provides a body portion having two jaw elements extending therefrom. The two jaw elements have securing blades for securing a needled suture. The securing blades cooperate with a first recess in each jaw element, and a releasing mechanism cooperates with the securing blades for releasing the needle secured by the securing blades. The two jaw elements are closed on soft tissue, allowing the needle to penetrate the soft tissue. The needle is transferred and secured from one jaw element to the other. The suture is pulled through the soft tissue creating a stitch therethrough. The suturing apparatus of Stone et al. provides a quicker method for suturing soft tissue than by suturing soft tissue by hand.

Stone et al. also provides a loading unit for use with the suturing apparatus to ensure rapid and positive placement of a suture within the jaw elements. The loading unit includes a support member in a position to be grasped by the jaw elements and a storage member for holding a length of suture attached to the needle. The loading unit provides a quick and repeatable method of loading a suture needle within the suturing apparatus.

It would be advantageous to have a suture anchor installation system having suture needles adapted for use with the suturing apparatus as disclosed in Stone et al. It would also be advantageous to provide a loading unit on the suture anchor installation system to provide a quick and efficient method of loading the suture apparatus with a suture needle.

SUMMARY

A suture anchor installation system includes a body portion having a distal end and a proximal end, an elongated shaft extending distally from the distal end of the body portion, the shaft having a distal end with an annular region disposed at the distal end of the shaft. A suture anchor is attachable within the annular region and comprises a setting portion and an engagement portion, the suture anchor having at least one suture associated therewith. A channel extends longitudinally down the distal end of the shaft being configured and dimensioned to receive the at least one suture extending form the suture anchor. A suture retaining member is positioned on the body portion, the suture retaining member including tabs to grip the at least one suture extending from the suture anchor to maintain the setting portion within the engagement portion.

A loading unit for use with a suturing apparatus is mountable on the body portion including a mounting member positioned on the body portion and configured to releasably hold at least one suture needle, the at least one suture needle being associated with the at least one suture extending from the suture anchor. The loading unit further includes a receiving structure formed in the body portion for receiving a distal end portion of the suturing apparatus in operative alignment with mounting member to facilitate mounting of the at least one surgical needle in the suturing apparatus.

In particularly preferred embodiments, the suture anchor installation system further comprises a slide attaching to the mounting member for repositionably mounting the mounting member on the body portion for positioning suture needles to facilitate mounting of the suture needles in the suturing apparatus. The body portion may define a cavity therein for storage of the at least one suture. Enclosing at least a portion of the cavity by installing a cover, the loading unit may be integrally mounted on the cover, and the at least one suture may be stored on spools rotatably disposed within the cavity of the body portion. The at least one suture may also be stored within tubes disposed within the cavity of the body portion. The suture anchor installation system may include a needle tray having a first suture needle and second suture needle releasably disposed thereon, the first suture needle and the second suture needle are configured transversely with respect to the needle tray to facilitate mounting of the needles in the suturing apparatus. A releasable locking mechanism may be included for securing the needle tray in a first loading position corresponding to a first suture needle or a second loading position corresponding to a second suture needle thereby allowing the first suture needle to be loaded by the suturing apparatus when the needle tray is locked in the first loading position and the second suture needle to be loaded when the needle tray is locked in the second loading position. At least two loading units having mounting members may be integrally formed on the body portion.

In still other preferred embodiments, the suture anchor installation system may have the receiving structure including a pair of spaced apart alignment tabs, the tabs guiding an elongate portion of the distal end portion of the suturing apparatus into position on the body portion for loading the at least one suture needle. A safety mechanism may be included on the loading unit, the safety mechanism preventing the removal of the suturing apparatus for the body portion prior to loading the at least one suture needle. The suture anchor installation system may include an outer tube disposed on the shaft, the outer tube being biased distally and providing support for the suture anchor at a distal end of the outer tube. The suture retaining member positioned on the body portion includes tabs to grip the at least one suture extending from the suture anchor to maintain the setting portion within the engagement portion, the tabs being released by inwardly moving extensions releasing grip on the at least one suture by proximally translating the outer tube relative to extensions; the extensions camming against a proximal end portion of the outer tube to release a compressive force developed between the tabs and suture guides.

Another suture anchor installation system includes a body portion having a distal end and a proximal end, an elongated shaft extending distally from the distal end of the body portion, the shaft having a distal end with an annular region disposed thereon for receiving a suture anchor, a suture retaining member positioned on the body portion, the suture retaining member including tabs for gripping an at least one suture, a loading unit for use with a suturing apparatus mountable on the body portion including mounting members positioned on the body portion and configured to releasably hold at least one suture needle, the mounting members integrally formed on the body portion and the loading unit further including receiving structures formed in the body portion for receiving a distal end portion of the suturing apparatus in operative alignment with the mounting members to facilitate mounting of surgical needles in the suturing apparatus.

In other embodiments, a suture anchor attachable within the annular region and comprising a setting portion and an engagement portion, the suture anchor having at least one suture associated therewith and the at least one suture extending from the suture anchor to maintain the setting portion within the engagement portion of the suture anchor may be included. The at least one suture needle may be associated with the at least one suture extending from the suture anchor. The body portion may include a cavity therein for storage of the at least one suture. A cover for enclosing at least a portion of the cavity may be included, the loading unit and mounting members being integrally disposed on the cover. The at least one suture may be stored on spools rotatably disposed within the cavity of the body portion. The at least one suture may be stored within tubes disposed within the cavity of the body portion. The mounting members may include a needle tray having a suture needle releasably disposed thereon and connected to the at least one suture, the suture needle being configured transversely with respect to the needle tray to facilitate mounting of the needles in the suturing apparatus. Two loading units may be formed on opposite ends of the body portion thereby allowing a first suture needle to be loaded by the suturing apparatus in one loading unit and a second suture needle to be loaded in the other loading unit. The receiving structure may include a pair of spaced apart alignment tabs forming a U-channel, the tabs guiding an elongate portion of the distal end portion of the suturing apparatus into position on the body portion for loading the at least one suture needle. A safety mechanism on the loading unit may be included. The safety mechanism prevents the removal of the suturing apparatus for the body portion prior to loading the at least one suture needle.

A method for applying a suture anchor comprises the steps of providing a body portion having a distal end and a proximal end, an elongated shaft extending distally from the distal end of the body portion, the shaft having a distal end with an annular region disposed at the distal end of the shaft, a suture anchor attachable within the annular region and comprising a setting portion and an engagement portion, the suture anchor having at least one suture associated therewith, a channel extending longitudinally down the distal end of the shaft being configured and dimensioned to receive the at least one suture extending from the suture anchor, a suture retaining member positioned on the body portion, the suture retaining member including tabs to grip the at least one suture expanding from the suture anchor to maintain the setting portion within the engagement portion, a loading unit for use with a suturing apparatus mountable on the body portion including a mounting member positioned on the body portion and configured to releasably hold at least one suture needle, the at least one suture needle being associated with the at least one suture extending from the suture anchor, and the loading unit further including a receiving structure formed in the body portion for receiving a distal end portion of the suturing apparatus in operative alignment with mounting member to facilitate mounting of the at least one surgical needle in the suturing apparatus; implanting the suture anchor into a bone; securing the suture anchor within the bone mounting the suture apparatus into the receiving structure of the loading unit; loading the at least one suture needle into the suturing apparatus; and suturing the suture anchor to soft tissue with the at least one suture needle.

In particularly preferred methods, the step of implanting the suture anchor comprises inserting the suture anchor and at least a portion of the annular region into a bore in the bone, engaging the bone with a distally biased outer tube disposed on the shaft such that the outer tube is retracted proximally when suture anchor and annular portion are advanced distally, and releasing the at least one suture from the grip of the tabs by camming extensions to release the tabs triggered by the proximal motion of the outer tube. The step of securing the suture anchor includes drawing the at least one suture proximally, camming the setting portion against the engagement portion of the suture anchor to cause the engagement portion to spread and engage the walls of a bore in the bone. The step of loading the at least one suture needle into the suturing apparatus includes presenting a first suture needle on a needle tray mounted on the mounting member, mounting the suturing apparatus onto the receiving structure of the loading unit and closing jaws at the distal end portion of the suturing apparatus onto the first suture needle to load the first needle for suturing. The following steps may also be included: presenting a second suture needle on a second needle tray mounted on a second mounting member, mounting the suturing apparatus onto a second receiving structure of a second loading unit disposed on the body portion and closing jaws at the distal end portion of the suturing apparatus onto the second suture needle to load the second needle for suturing. The method for applying a suture anchor further comprises the step of adjusting the slide to position a second suture needle for loading onto the suturing apparatus.

BRIEF DESCRIPTION OF THE DRAWINGS

Various embodiments are described herein with reference to the drawings, wherein:

FIG. 17 is an enlarged perspective view of the suture anchor being installed in the distal end of the inner shaft of FIG. 10;

FIG. 18 is an enlarged perspective view of the suture anchor installed in the distal end of the inner shaft of FIG. 10 with the suture disposed in grooves;

FIG. 19 is an enlarged perspective view of the suture anchor installed in the distal end of the inner shaft of FIG. 10 and the outer tube of FIG. 12;

FIG. 20 is a perspective view of a cannula;

FIG. 21 is a perspective view of an obturator;

FIG. 22 is an exploded perspective view of a bone drill and a sleeve;

FIG. 23 is a cross-sectional view of the obturator and sleeve entering the cannula;

FIG. 24 is a cross-sectional view of the cannula with obturator and sleeve therein;

FIG. 25 is a cross-sectional view of the cannula with the bone drill disposed therein and showing a bore drilled in a bone;

FIG. 26 is a cross-sectional view of the cannula with the suture anchor installation system disposed therein and the suture anchor disposed in the bore drilled into the bone;

FIG. 29 is an enlarged cross-sectional view of the cannula with the suture anchor installation system removed and the suture anchor disposed in the bore drilled into the bone;

FIG. 30 is an enlarged perspective view of the suture anchor of FIG. 16 having the engagement portion unexpanded;

FIG. 31 is an enlarged cross-sectional view of the suture anchor disposed in the bore drilled into the bone and having a suture tensioned;

FIG. 32 is an enlarged perspective view of the suture anchor of FIG. 16 having the engagement portion expanded;

FIG. 41 is a cross-sectional view of the cover of FIG. 7 showing a button being depressed to release a slide from a first position;

FIG. 42 is a cross-sectional view of the cover of FIG. 7 showing the slide being translated and the button released to lock slide in second position;

DETAILED DESCRIPTION OF PREFERRED EMBODIMENTS

The present disclosure describes a suture anchor installation system and method having a loading unit disposed thereon. Loading unit provides at least one suture needle for loading the suture needle into a suturing apparatus. After a hole is predrilled into a bone, a suture anchor which has a suture prethreaded therethrough is introduced into the bone and frictionally engages walls of the hole. The suture has two ends. Each end is attached to a suture needle disposed on a base of the suture installation system. A first suture needle is located at a predetermined distance from a locating pin. When the suturing apparatus is installed on the locating pin, the first suture needle is positioned to be received by jaw elements of the suturing apparatus. Once loaded in the suturing apparatus, suturing of soft tissue may be performed. A second suture needle can be positioned to be received by the jaw elements of the suturing apparatus by translating a slide on which the suture needles are releasably mounted. Once appropriately positioned the second suture needle may be loaded into the suturing apparatus and soft tissue suturing may be performed.

Figure 1:
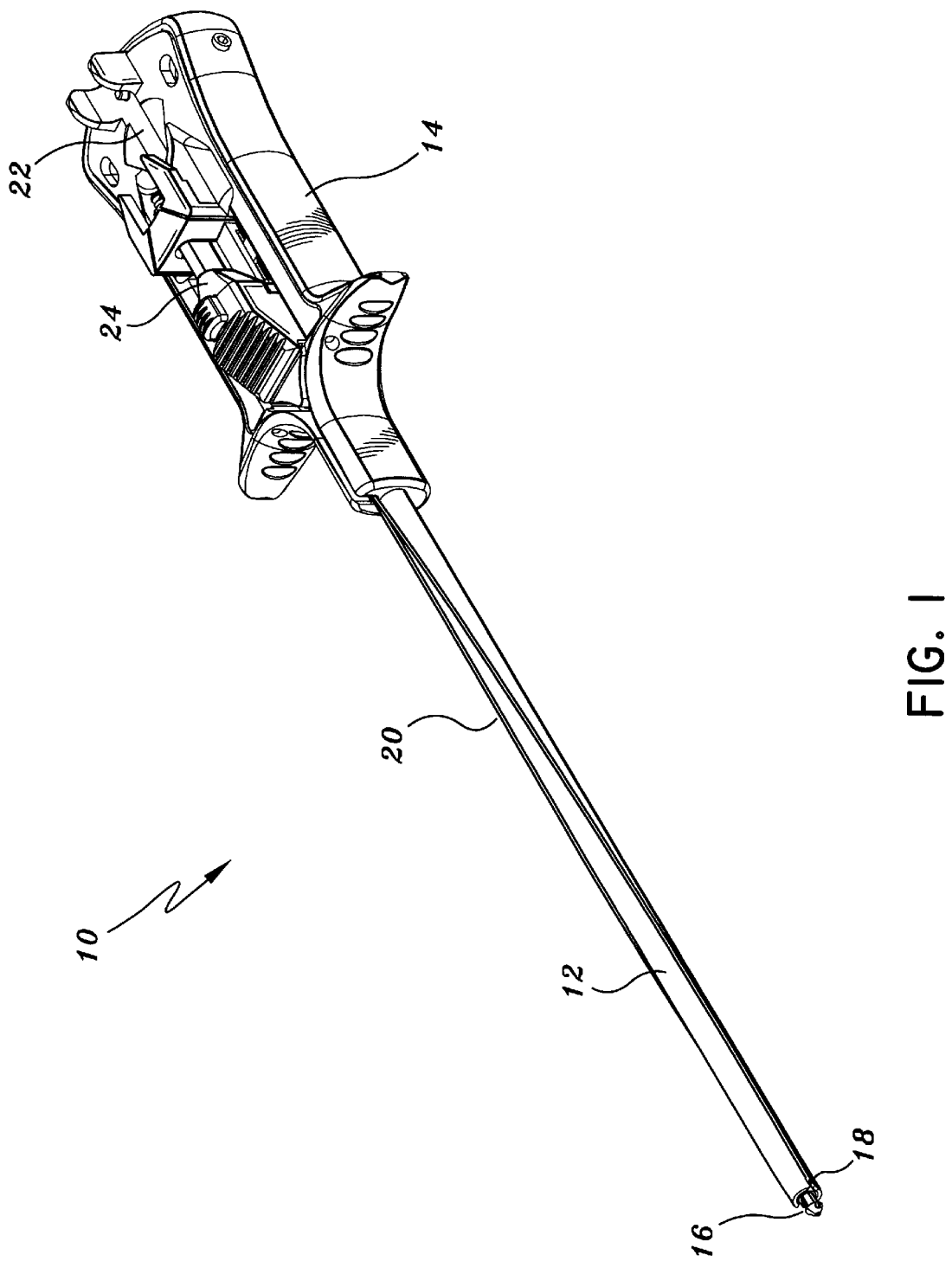
FIG. 1 is a perspective view of a suture anchor installation system.

Referring now in specific detail to the drawings in which like reference numerals identify similar or identical elements throughout the several views, and initially to FIG. 1, one embodiment of a suture anchor installation system is shown generally as assembly 10. Assembly 10 includes a body portion 14 and an elongated shaft portion 12 extending distally from body portion 14. A suture anchor 16 is shown within a distal end 18 of shaft portion 12. A suture 20 is threaded through suture anchor 16. Suture 20 is routed over shaft portion 12 and into body portion 14. Body portion 14 has a loading unit 22 and a slide 24 disposed thereon. Further description of each part is described herein.

Figure 2:
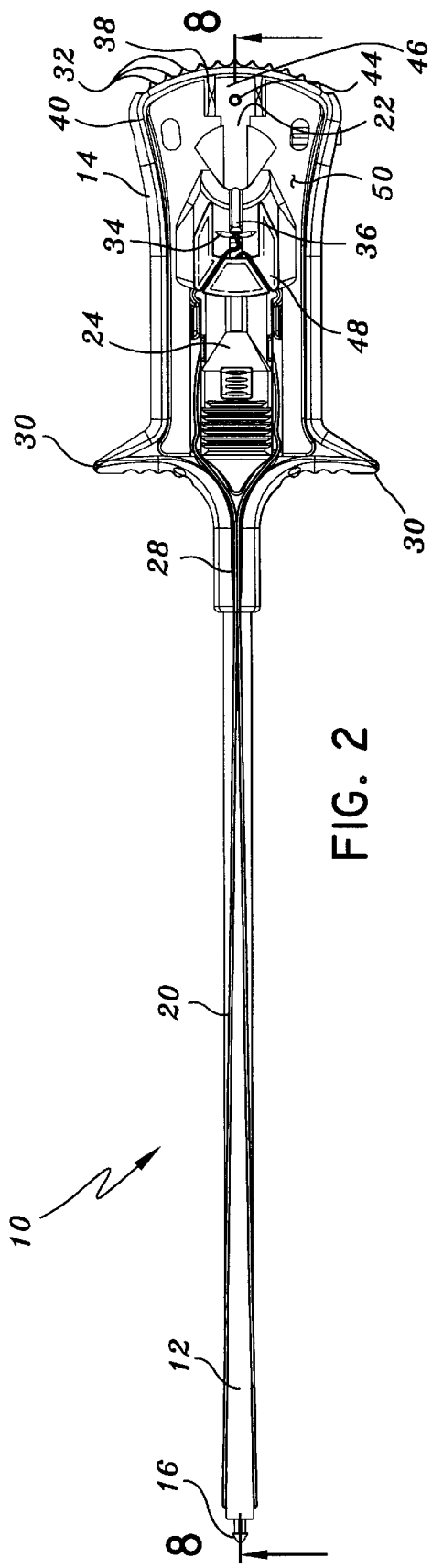
FIG. 2 is a top view of the suture anchor installation system of FIG. 1.
Figure 3:
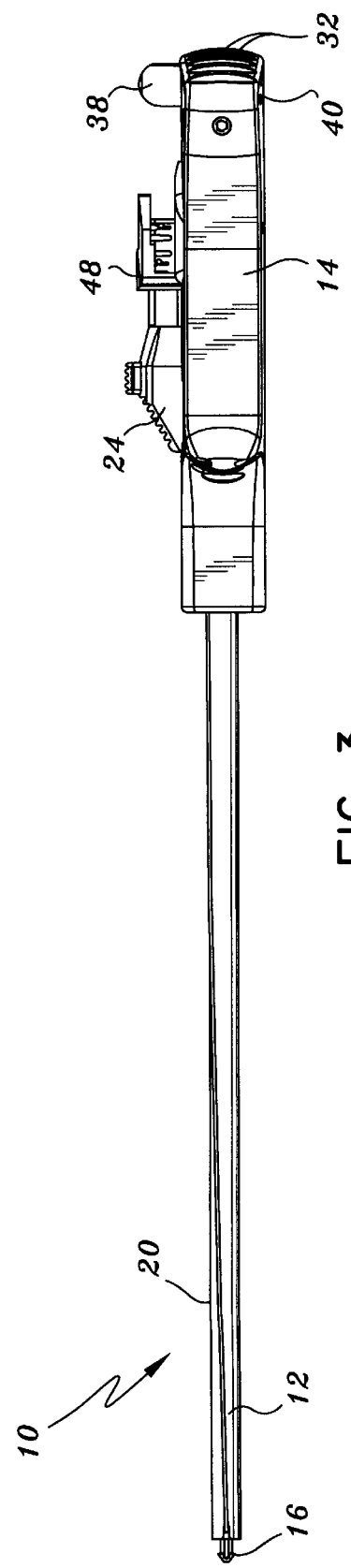
FIG. 3 is a side view of the suture anchor installation system of FIG. 1.

Referring to FIGS. 2 and 3, a distal end portion 26 of body portion 12 defines a suture channel 28 therethrough. Suture 20 extends through channel 28 and around slide 24. Body portion 14 is contoured to be easily manipulated by hand. Extensions 30 and ridges 32 are formed in body portion 14 to allow a surgeon to apply a force distally to insert suture anchor 16 during surgery. A first suture needle 34 is shown mounted on a suture holder 36. Loading unit 22 includes a U-channel 38 on a proximal end portion 40 of body portion 14 mounted on a cover 50. U-channel 38 has a locating pin 44 disposed at a bottom portion 46 of U-channel 38. Loading unit 22 further includes a needle dispenser portion 48 which is mounted on cover 50 and spaced apart a predetermined distance from U-channel 38. Loading unit 22 is used for mounting and loading needles for suturing.

Figure 4:
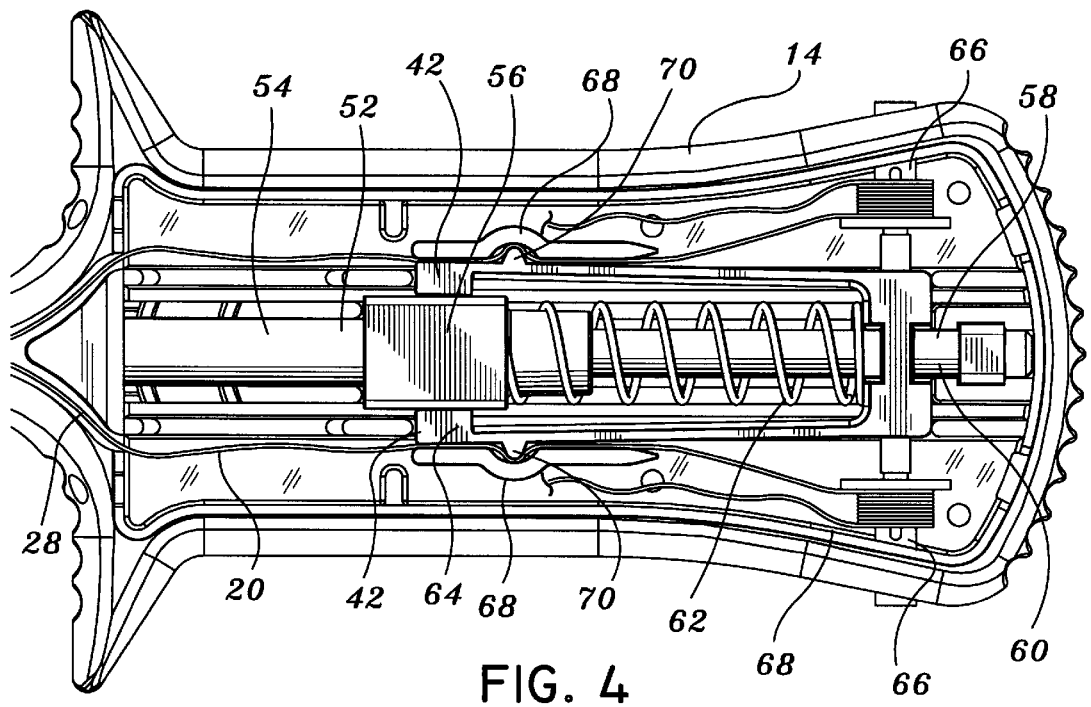
FIG. 4 is an enlarged top view of a body portion of the suture anchor installation system with a cover removed.
Figure 7:
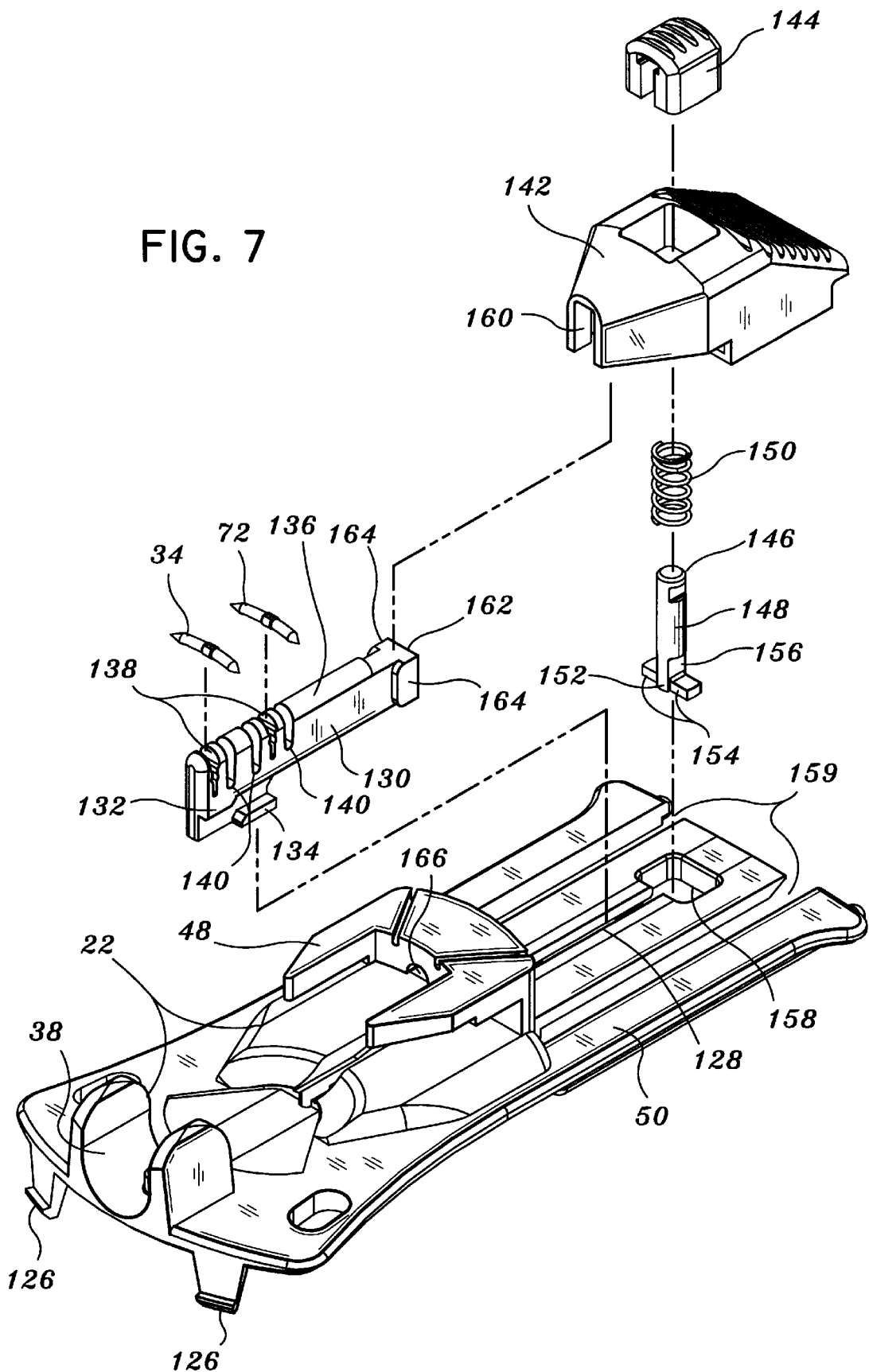
FIG. 7 is an exploded perspective view of the cover of the body portion.

Referring to FIG. 4, cover 50 is removed. A proximal end portion 52 of an outer tube 54 is shown and received within a support block 56. A proximal end portion 58 of an inner shaft 60 is disposed within outer tube 54 and rigidly mounted to body portion 14. Outer tube 54 is distally biased by a spring 62 disposed within a spring housing 64. Spring 62 engages support block 56 and spring housing 64 such that a bias force is applied against outer tube 54 through support block 56. Suture 20 is routed around spring housing 64 and stored on spools 66 rotatably mounted between an interior wall 68 of body portion 14 and spring housing 64. Exiting suture channel 28, suture 20 is routed between spring housing 64 and guides 68 and secured beneath tabs 70. Extensions 42 engage support block 56 deflecting tabs 70 toward guides 68 and gripping suture 20 therebetween. When support block 56 and therefore outer tube 54 are retracted proximally extensions 42 are released thereby releasing suture. Suture 20 further extends to spools 66 where a portion of suture 20 is stored thereon. Suture 20 extends from spools 66 and is attached to first suture needle 34 and a second suture needle 72 (FIG. 7).

Figure 5:
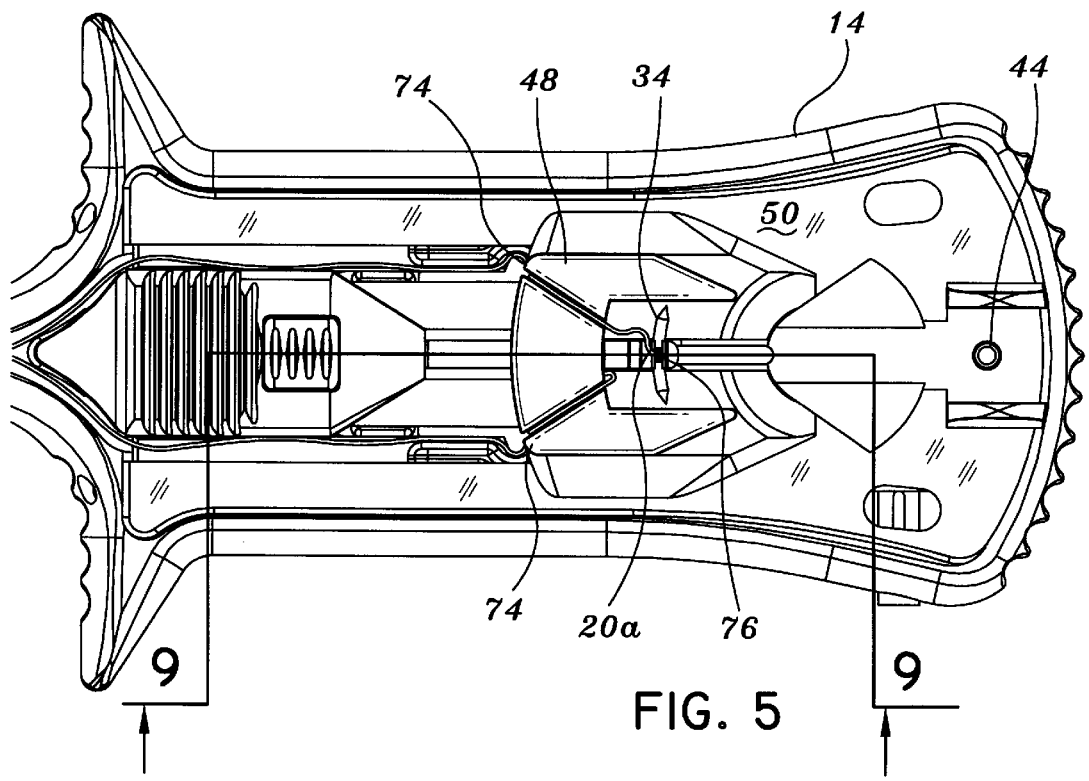
FIG. 5 is an enlarged top view of the body portion of FIG. 4 with the cover replaced.

Referring to FIG. 5, top cover 50 is shown on body portion 14. Suture 20 extends from spools 66 over needle dispenser portion 48. Needle dispenser portion 48 includes suture guides 74 formed therein. Suture 20 is a single length of material having two ends 20a and 20b (not shown). End 20a attaches to a middle portion 76 of first suture needle 34.

Figure 6:
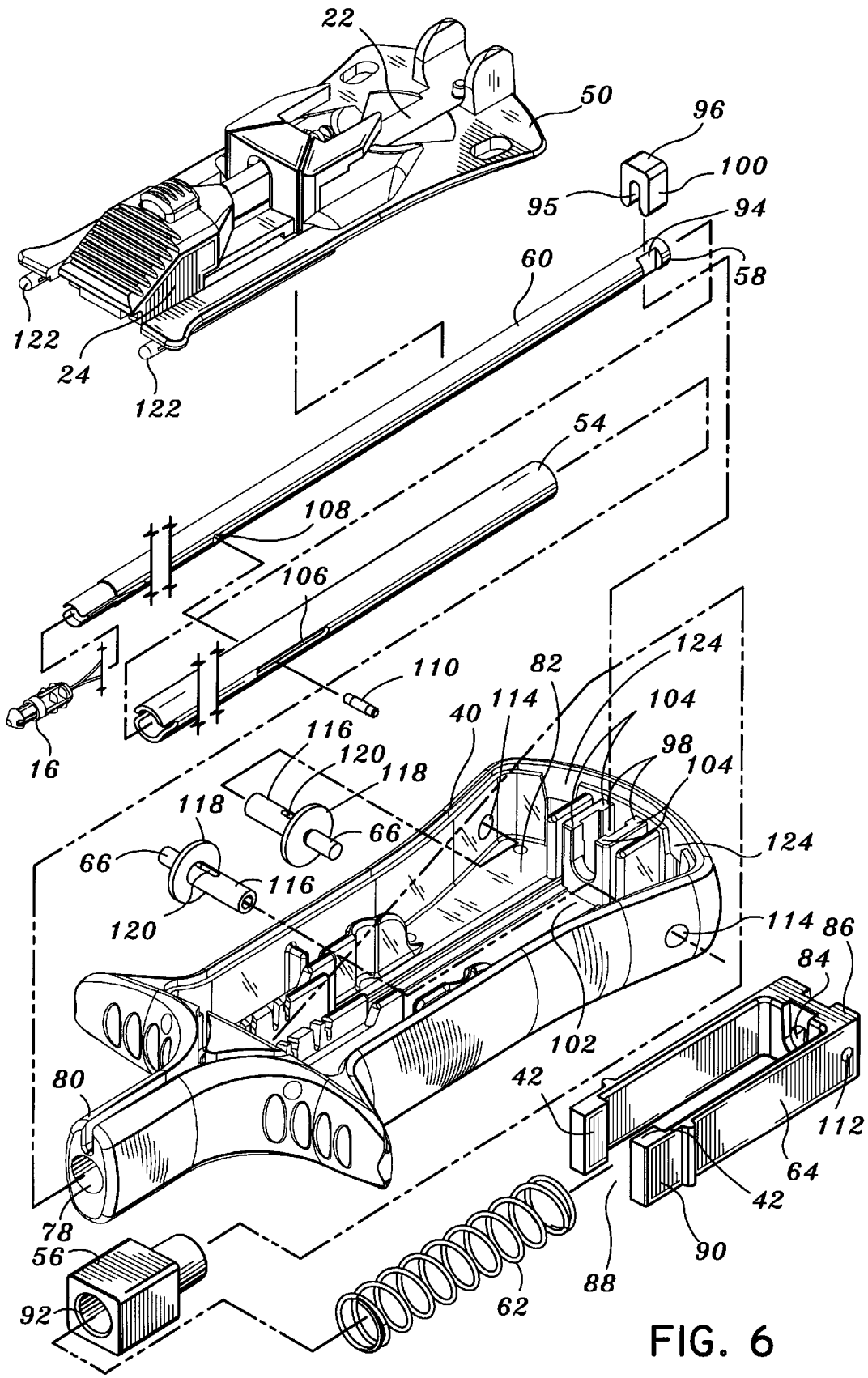
FIG. 6 is an exploded perspective view of the suture anchor installation system of FIG. 1.

Referring to FIG. 6, inner shaft 60 is disposed within outer tube 54. Body portion 14 defines a bore 78 through a distal end portion 80. Body portion 14 also defines a cavity 82 which is enclosed when cover 50 is installed. Cavity 82 communicates with bore 78. Inner shaft 60 and outer tube 54 are received in bore 78 and cavity 82. Inner shaft 60 extends through cavity 82 to proximal end portion 40 of body portion 14. Spring housing 64 has a bore 84 through a proximal end 86 and an open portion 88 at a distal end 90. Extensions 42 extend inwardly into open portion 88 on spring housing 64. Extensions 42 engage support block 56 while outer tube 54 is distally disposed. Prior to use tabs 70 and guides grip suture 20 and assist in maintaining suture anchor 16 in a secured position.

Support block 56 also defines a bore 92 therethrough. When assembled, inner shaft 60 is disposed within bore 78 of body portion 14, bore 92 of support block 56, spring 62 and bore 84 and opening 86 in spring housing 64.

Flats 94 are formed at proximal end portion 58 of inner shaft 60. A C-shaped member 96 is dimensioned and configured to engage flats 94 on interior surfaces 95 of C-shaped member 96 and be received within lateral supports 98 on exterior surfaces 100 of C-shaped member 96. Lateral supports 98 extend from a bottom interior surface 102 at proximal end portion 40 of body portion 14. Lateral supports 98 have extensions 104 extending inwardly. Inner shaft 60 is received between lateral supports 98 and C-shaped member 96 is secured therebetween. C-shaped member 96 prevents rotation and translation of inner shaft 60 by engaging extensions 104 and lateral supports 98.

Outer tube 54 is disposed about inner shaft 60. Outer tube 54 has a slot 106 formed longitudinally therein. Inner shaft 60 has a hole 108 corresponding to slot 106 which receives a pin 110 therethrough. Slot 106 and pin 110 cooperate to limit displacement of outer tube 54 which can translate with respect to inner shaft 60. Outer tube 54 is received through bore 78 of body portion 14 and bore 92 of support block 56. Support block 56 is rigidly attached to outer tube 54. Spring 62 distally biases support block 56 and therefore outer tube 54.

Spring housing 64 has a pair of holes 112 (one hole not shown) formed therein. Body portion 14 has a pair of openings 114 therein which are associated with pair of holes 112 when spring housing 64 is installed in body portion 14. Spools 66 have a shaft portion 116 and a wheel 118. Shaft portions 116 are received within holes 112 and openings 114 allowing spools 66 to rotate therein. Each shaft portion 116 has an opening 120 for receiving suture 20 to aid in winding suture 20 thereabout. Cover 50 has pins 122 extending distally therefrom for securing cover 50 to body portion 14. Body portion 14 has recesses 124 formed therein for receiving tabs 126 (see FIG. 7).

Referring to FIG. 7, needle dispenser portion 48 and U-channel 38 of loading unit 22 are integrally formed in cover 50. Cover 50 has a slot 128 defined therein. Slot 128 receives a needle tray 130 therein. Needle tray 130 slides within slot 128 and is secured by top surface tabs 132 and bottom surface tabs 134. Needle tray 130 has a top portion 136 having a pair of needle notches 138 for receiving and securing first needle 34 and second needle 72 therein. Relief notches 140 are disposed adjacent to needle notches 138 to provide compliance to needle notches 138 and to allow first needle 34 and second needle 72 to be inserted and removed therefrom. Slide 24 includes a housing portion 142 which is dimensioned and configured to receive a button 144 therein. Button 144 attaches to a first end portion 146 of a rod 148. A spring 150 is disposed on rod 148. A second end portion 152 of rod 148 has extensions 154. Second end portion 152 of rod 148 has a recessed flat portion 156 formed therein to be received and secured in slot 128. Spring 150 is mounted on rod 148 and biases rod 148 upward in order to return button 144 to an initial upward position.

Cover 50 has an opening 158 therethrough. Opening 158 allows space so that tabs 134 of needle tray 130 and extensions 154 of rod 148 may be accommodated to allow placement within slot 128. Cover 50 has slots 159 for allowing deployment of suture 20 during a surgical procedure.

Housing 142 defines an aperture 160 for receiving and attaching a distal end portion 162 of needle tray 130. Distal end portion 162 of needle tray 130 has a step 164 formed thereon that is dimensioned and configured to be received within aperture 160. Distal end portion 162 is secured within housing 142 such that housing 142 and needle tray 130 may be translated simultaneously within slot 128. Needle dispensing portion 48 has an open portion 166 to allow needle tray 130 to pass therethrough when disposed within slot 128.

Figure 8:
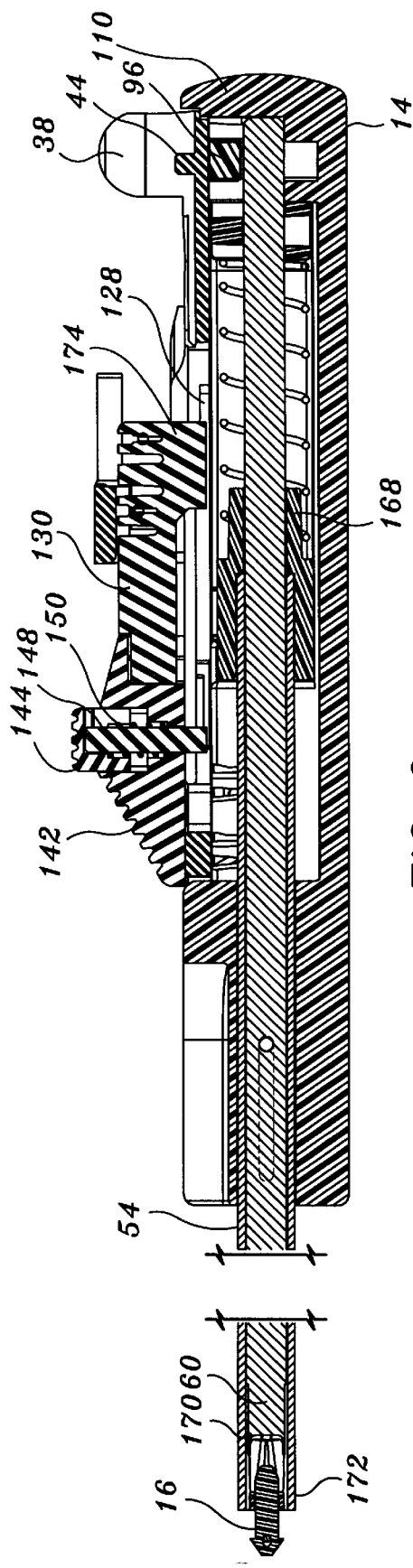
FIG. 8 is a cross-sectional view taken along section lines 8—8 of FIG. 2.

Referring to FIG. 8, inner shaft 60 is disposed within outer tube 54, and outer tube 54 is received within support block 56. Support block 56 has a proximal end portion 168 which is disposed within spring 62 in order to bias outer tube 54 distally. When suture anchor 16 is loaded at a distal end portion 170 of inner shaft 60, a distal end portion 172 of outer tube 54 encloses a portion of suture anchor 16 therein when outer tube 54 is distally advanced to aid in retaining suture anchor 16 therein. Inner shaft 60 extends through body portion 14 and is secured at proximal end portion 40 by C-shaped member 96.

A lower portion 174 of needle tray 130 is shown disposed within slot 128. Needle tray 130 attaches to housing 142 and extends below needle dispensing portion 48 of loading unit 22. Button 144 is attached to rod 148. Rod 148 has extensions 154 disposed within slot 128. Rod 148 is biased upward by spring 150 to maintain button 144 out of housing 142. U-channel 38 has locating pin 44 disposed therein.

Figure 9:
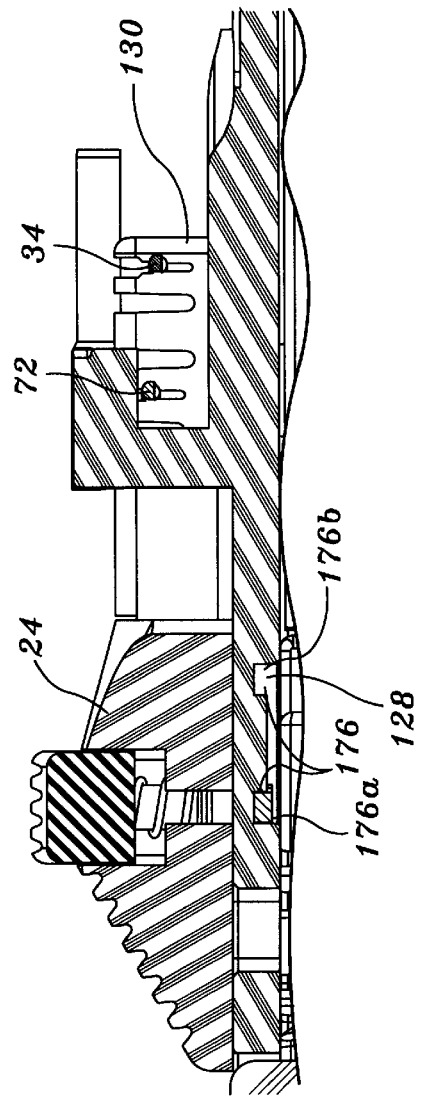
FIG. 9 is a n enlarged cross-sectional view taken along section lines 9—9 of FIG. 5.

Referring to FIG. 9, an enlarged cross sectional view of slide 24 and needle tray 130 is shown. Slot 128 has two recess portions 176. A first recess portion 176a corresponds to a first location of needle tray 130. First location presents first needle 34 for loading. A second recess portion 176b corresponds to a second location of needle tray 130. Second location presents second needle 72 for loading. Spring 150 biases rod 148 such that extensions 154 fit within recesses 176 thereby maintaining slide 24 and needle tray 130 in either the first location or second location.

Figure 10:
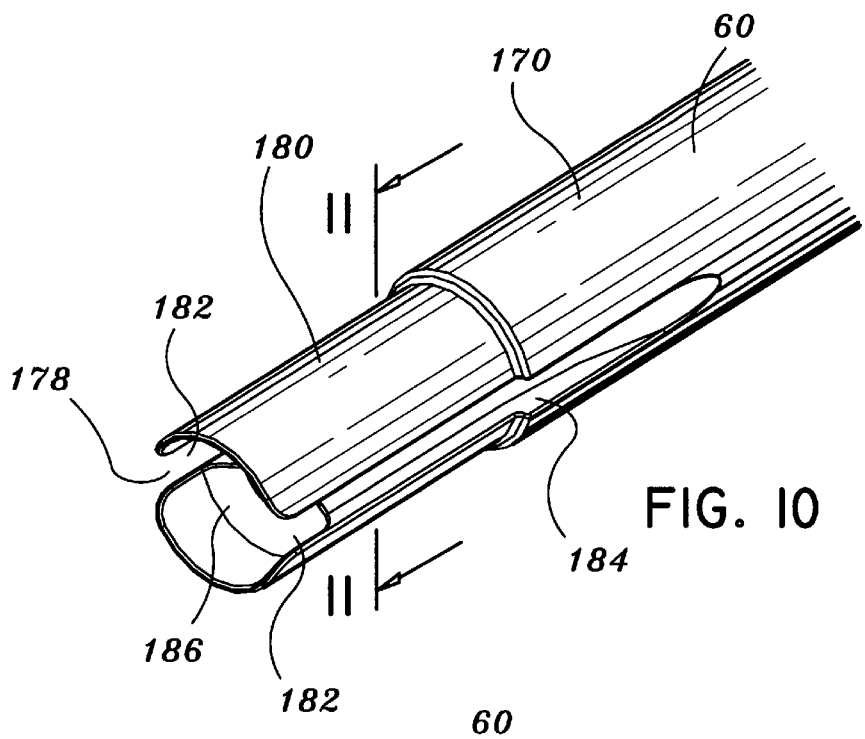
FIG. 10 is an enlarged perspective view of a distal end of an inner shaft.
Figure 11:
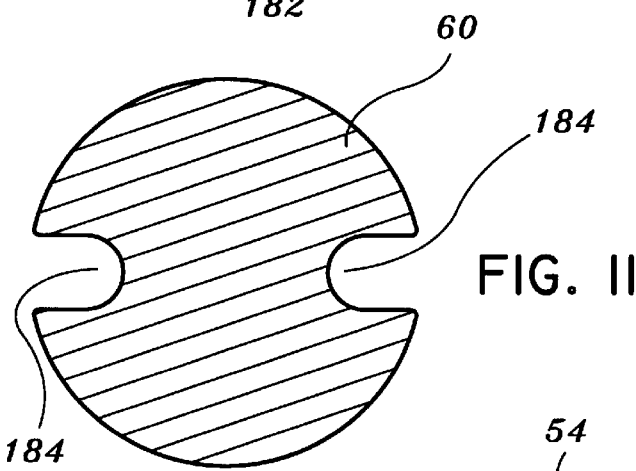
FIG. 11 is a cross-sectional view taken along section line 11—11 of FIG. 10.
Figure 12:
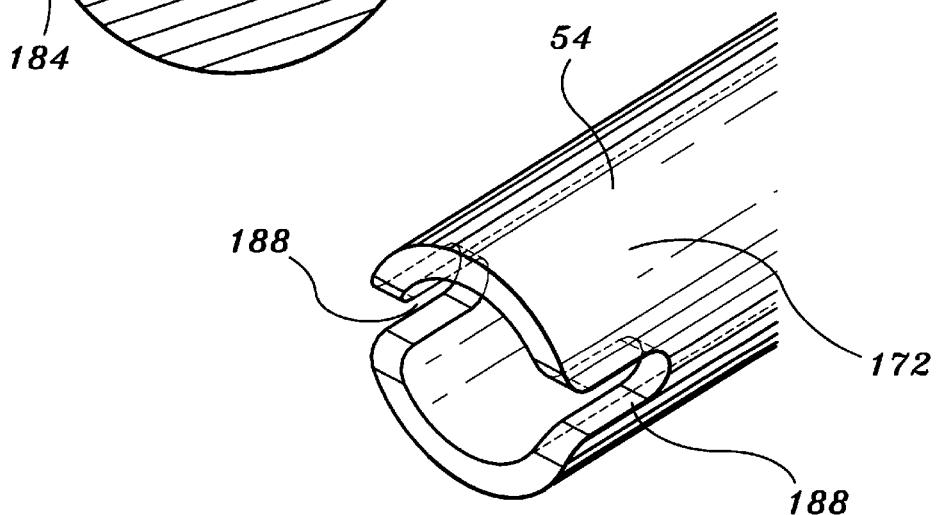
FIG. 12 is an enlarged perspective view a distal end of an outer tube.

Referring to FIGS. 10 and 11, distal end portion 170 of inner shaft 60 is shown. Distal end portion 170 has an annular region 178 formed therein. Annular region 178 has a reduced outer diameter portion 180. Annular region 178 has notches 182 in communication with grooves 184 formed within inner shaft 60. Notches 182 and grooves 184 are for receiving suture 20 (FIG. 18). A bearing surface 186 is disposed on inner shaft 60 for applying an insertion force against suture anchor 16 during installation. As shown in FIG. 12, distal end portion 170 of outer tube 54 has notches 188 for receiving suture 20 therein. Notches 188 in outer tube 54 correspond to notches 182 and grooves 184 in inner shaft 60. Notches 182 and 188 and grooves 184 allow suture 20 to be routed along outer 54 to body portion 14.

Figure 13:
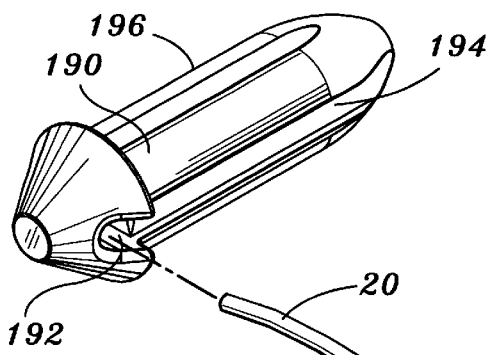
FIG. 13 is an enlarged perspective view of a setting portion of a suture anchor and a suture.
Figure 14:
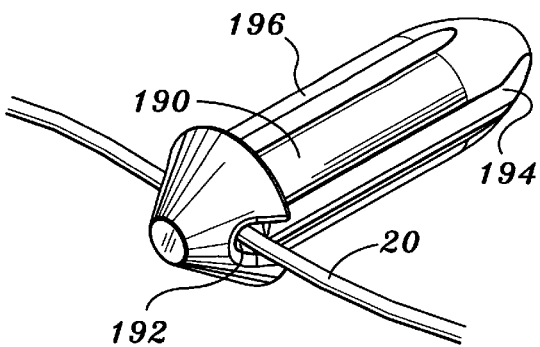
FIG. 14 is an enlarged perspective view of the setting portion of the suture anchor having the suture threaded therethrough.

Referring to FIGS. 13 and 14, a setting portion 190 of suture anchor 16 has a hole 192 therethrough substantially perpendicular to a longitudinally axis. Suture channels 194 extend longitudinally along an exterior surface 196. Suture 20 is threaded through hole 192.

Figure 15:
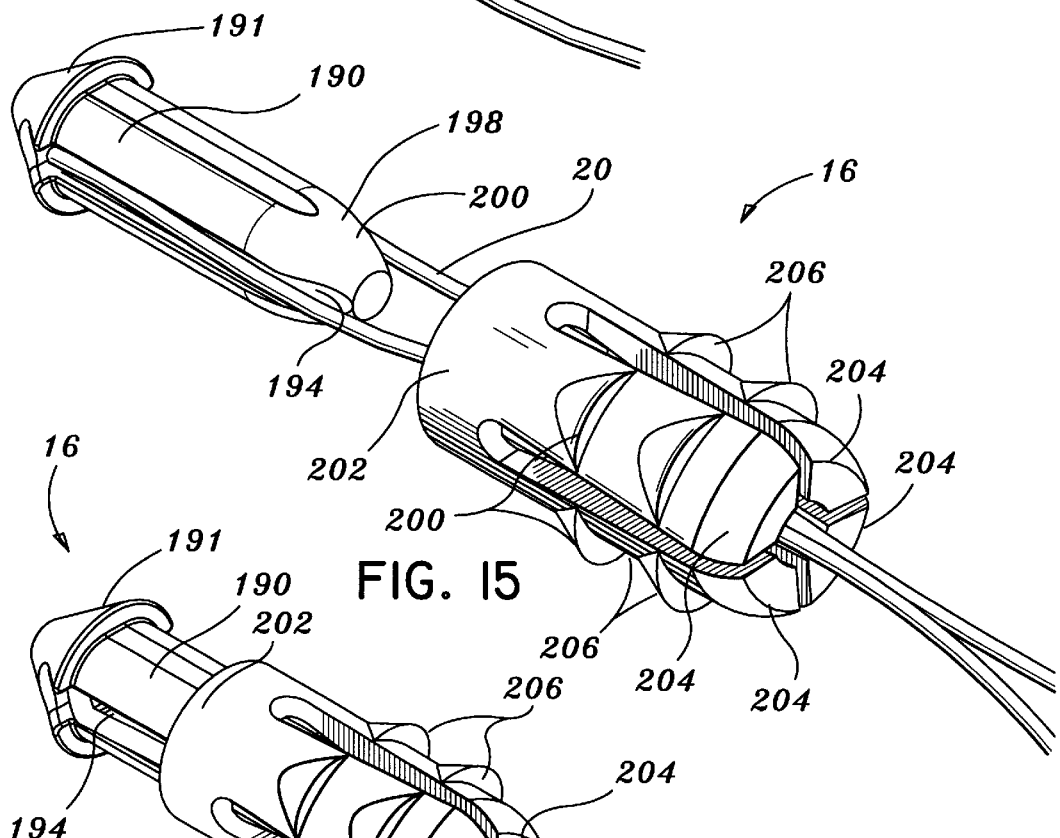
FIG. 15 is an enlarged perspective view of the setting portion FIG. 14 being installed into a engagement portion.
Figure 16:
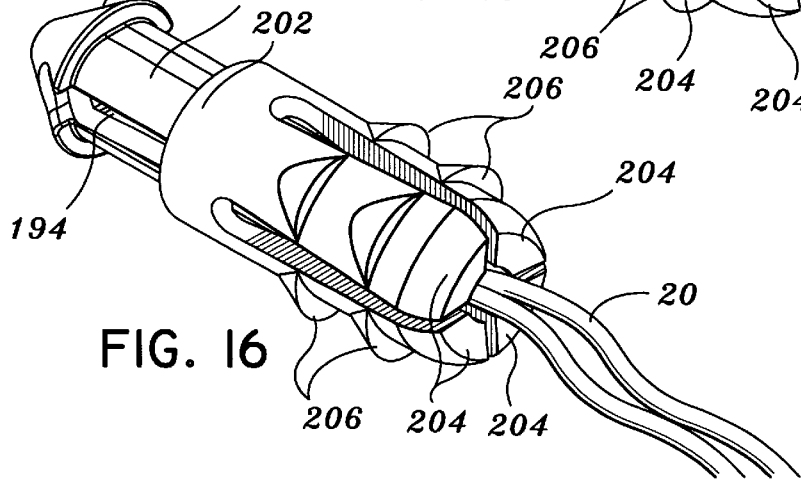
FIG. 16 is an enlarged perspective view of the suture anchor.

Referring to FIGS. 15 and 16, suture 20 is placed within suture channels 194 passing over a camming surface 198 disposed on a proximal end portion 200 of setting portion 190. Suture 20 is passed through an engagement portion 202 of suture anchor 16. Engagement portion 202 has a plurality of legs 204, preferably four legs. Legs 204 have barbs 206 formed thereon. Setting portion 190 is inserted into engagement portion 202 and is ready to be loaded onto distal end portion 170 of inner shaft 60 (FIG. 8). A head 191 of setting portion 190 is dimensioned and configured to engage engagement portion 202 to prevent setting portion from moving through engagement portion 202.

Referring to FIGS. 17 and 18, suture 20 is oriented substantially perpendicular to the longitudinal axis of suture anchor 16. Engagement portion 202 is compressed radially inward and placed within annular region 178 on distal end portion 170 of inner shaft 60. The resiliency of engagement portion 202 provides an outward biasing force to frictionally maintain engagement portion 202 within annular region 178. Outer tube 54 (FIG. 19) is retracted proximally to expose grooves 184 on inner shaft 60. Suture 20 is folded over itself and stowed within grooves 184.

Referring to FIG. 19, outer tube 54 is advanced distally. Notches 188 in distal end portion 172 of outer tube 54 receive suture 20 therein and a remaining portion of suture 20 is stowed as described above for FIGS. 1–5. Outer tube 54 is advanced distally to surround a large portion of engagement portion 202 of suture anchor 16. Outer tube 54 provides additional support to aid in maintaining suture anchor 16 within annular region 178.

A cannula 206 is shown in FIG. 20 for use in maintaining access to an operative site during surgery. FIG. 21 shows an obturator 208. Obturator 208 has a pointed end 210 and a knurled wheel 212 opposite pointed end 210. FIG. 22 shows a sleeve 214 having a longitudinal bore 216 therethrough. A handle 218 is attached to sleeve 214 for aiding a surgeon in maintaining sleeve 214 in an operative position during surgery. A distal end 220 of sleeve 214 has barbs 222 extending therefrom. A proximal end portion 224 of sleeve 214 funnels into bore 216 of sleeve 214 and can receive either obturator 208 or a bone drill 226 therein for surgery. Bone drill 226 is dimensioned and configured to fit and rotate within sleeve 214. A drill bit 228 is inserted into a distal end 230 of bone drill 228. An attachment portion 232 is adapted to connect with a drive motor (not shown) for rotating drill bit 228.

Referring to FIG. 23, cannula 206 is inserted into an incision 234 (FIG. 24). Cannula 206 has an elastomeric seal 236 having an opening 238 therein at a proximal end portion 240 of cannula 206. Obturator 208 is inserted into bore 216 of sleeve 214 and is inserted therethrough. Pointed tip 210 of obturator 208 leads sleeve 214 through elastomeric seal 236 of cannula 206.

Referring to FIG. 24, obturator 208 and sleeve 214 are advanced together distally through cannula 206 and into tissue 236. Obturator 208 opens a path in tissue 236 so that sleeve 214 may be inserted deep enough into a patient to contact bone 238 (FIG. 25).

Referring to FIG. 25, barbs 222 on distal end 220 of sleeve 214 contact bone 238 and provide frictional engagement to aid in preventing movement parallel to the surface of the bone 238 during drilling. Obturator 208 is removed from sleeve 214 and bone drill 226 is introduced. Drill bit 228 is used to create a bore 240 in bone 238. Done drill 226 is removed from sleeve 214 after bore 240 is drilled then sleeve 214 is removed form cannula 206.

Figure 27:
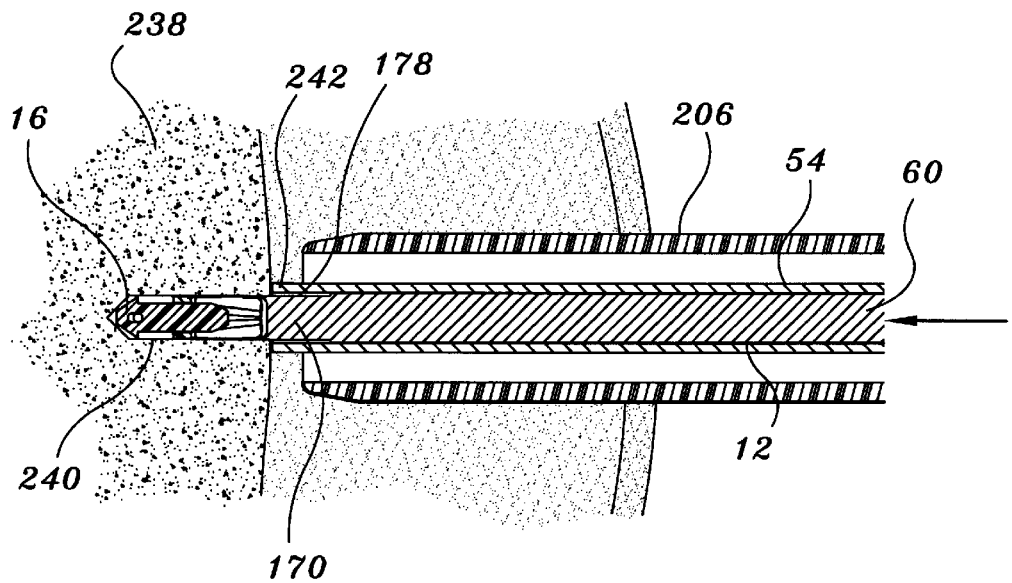
FIG. 27 is an enlarged cross-sectional view of the cannula with the suture anchor installation system disposed therein and the suture anchor disposed in the bore drilled into the bone.
Figure 28:
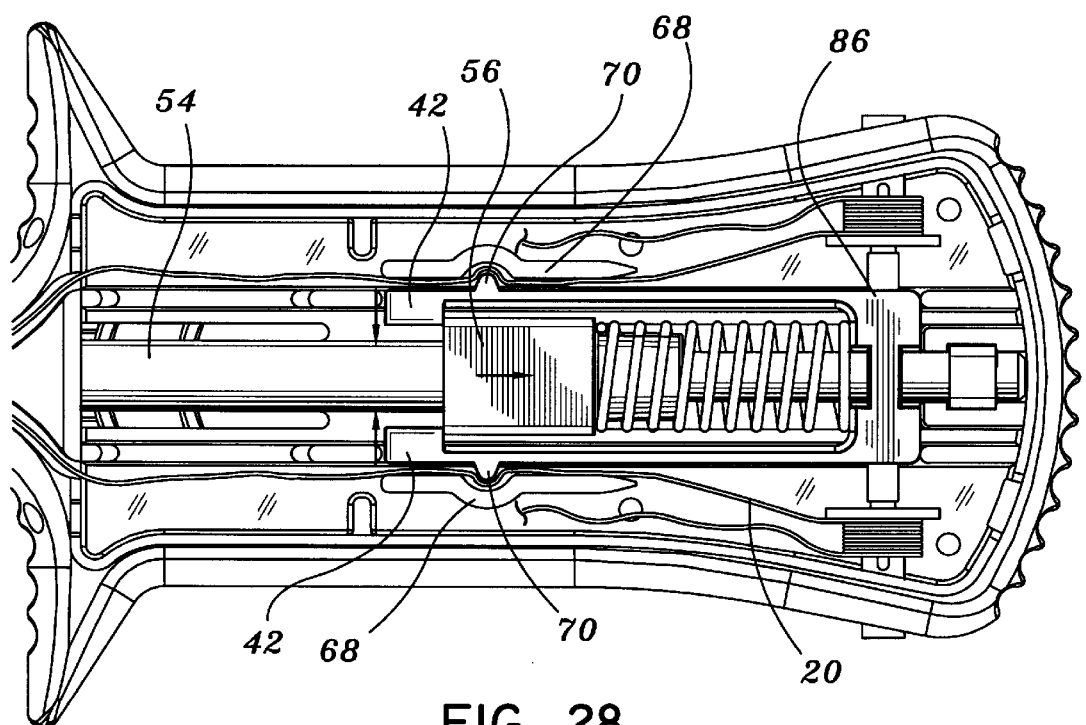
FIG. 28 is an enlarged top view of the body portion of FIG. 4 showing a support block being retracted and extensions moving inwardly.

Referring to FIGS. 26 and 27, assembly 10 has shaft portion 12 inserted into cannula 206. A portion of suture anchor 16 is placed into bore 240 in bone 238. Outer tube 54 engages bone 238 at a distal end 242. Inner shaft 60 is further advanced distally and annular region 178 enters at least a portion of bore 238 in order to allow suture anchor 16 to be inserted. As annular region 178 is inserted into bore 240, distal end 242 of outer tube 54 remains in contact with bone 238. As shown in FIG. 28, when a predetermined depth is reached by suture anchor 16, support block 56 which is rigidly attached to outer tube 54 moves proximally beyond extensions 42 in spring housing 86. Extensions 42 move inwardly retaining support block 56 and outer tube 54 in a proximally retracted position. This position releases suture 20 from the stowed position in grooves 184 at distal end portion 170 of inner shaft 60. Further, suture 20 may now be released from between tabs 70 and guide 68.

Referring to FIG. 29, shaft portion 12 (FIG. 27) is removed from cannula 206 leaving suture anchor 16 disposed within bore 240 and having suture 20 threaded therethrough. Engagement portion 202 is in an unexpanded position after suture anchor 16 has been positioned within the bore 240. The unexpanded position of suture anchor 16 is shown in FIG. 30.

Referring to FIGS. 31 and 32, suture 20 is tensioned retracting setting portion 190 proximally relative to engagement portion 202. Camming surface 198 of setting portion 190 causes legs 204 of engagement portion 202 to be biased radially outward. Outward biasing of legs 204 causes barbs 206 to frictionally engage an inner surface 244 of bore 240 thereby anchoring suture anchor 16 within bore 240.

Figure 33:
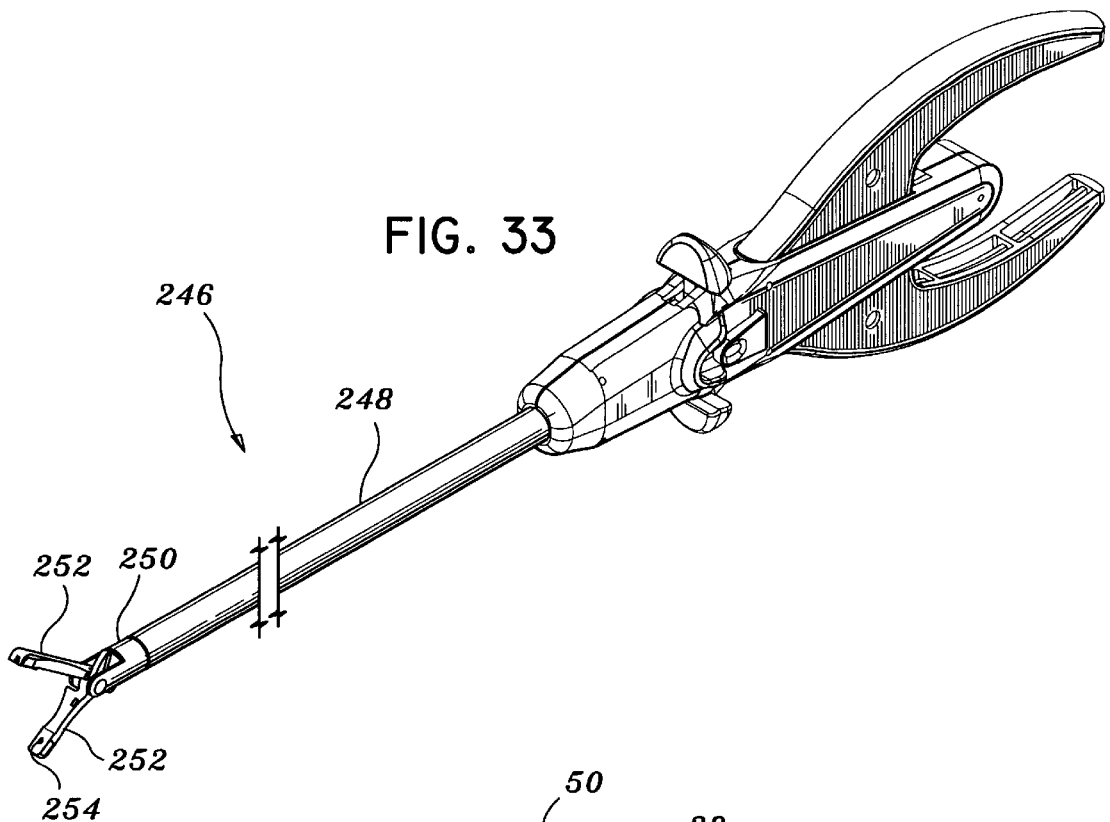
FIG. 33 is a perspective view of a suturing apparatus.

Referring to FIG. 33, a surgical suturing apparatus 246 is shown. The structure and operation of suturing apparatus 246 is described in U.S. Pat. No. 5,478,344 to Stone et al. and is incorporated herein by reference. Suturing apparatus 246 includes an elongated tubular member 248 having a distal end portion 250. Distal end portion 250 has a pair of jaw elements 252 pivotally attached thereto. Each jaw 252 has a recess 254 formed therein dimensioned and configured to receive a suture needle (not shown).

Figure 34:
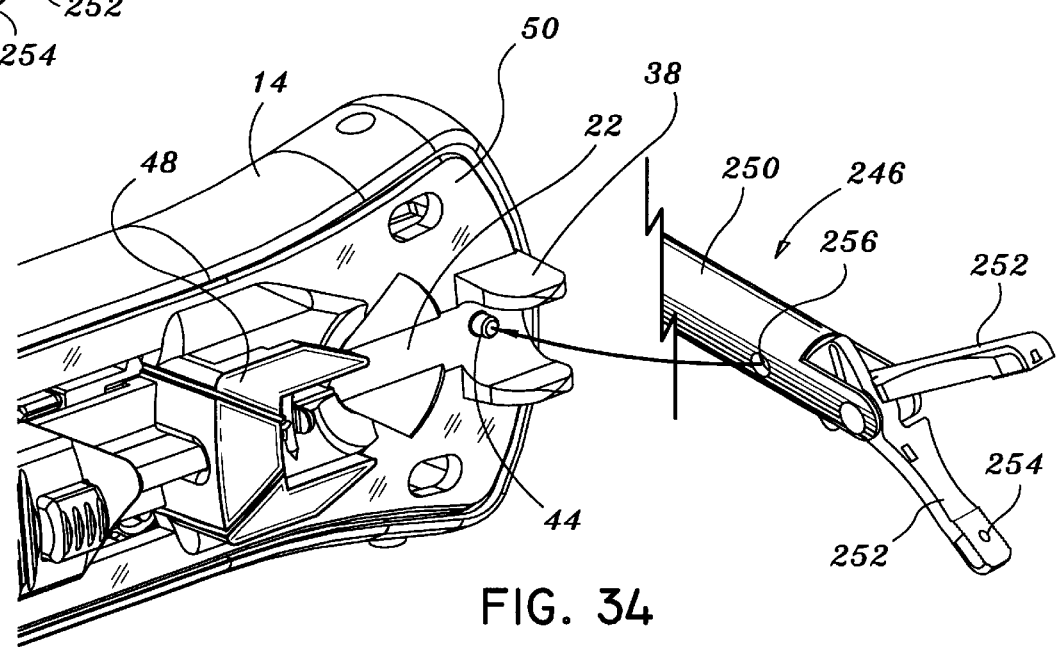
FIG. 34 is an enlarged perspective view of the suturing apparatus of FIG. 33 being loaded into a loading unit on the cover of the body portion.

Referring to FIG. 34, loading unit 22 is formed on cover 50 of body portion 14. Distal end portion 250 has a hole 256 formed therein. Hole 256 is dimensioned and configured to receive locating pin 44 disposed within U-channel 38 of loading unit 22. Locating pin 44 ensures the proper placement of jaw elements 252 relative to needle dispensing portion 48 of loading unit 22.

Figure 35:
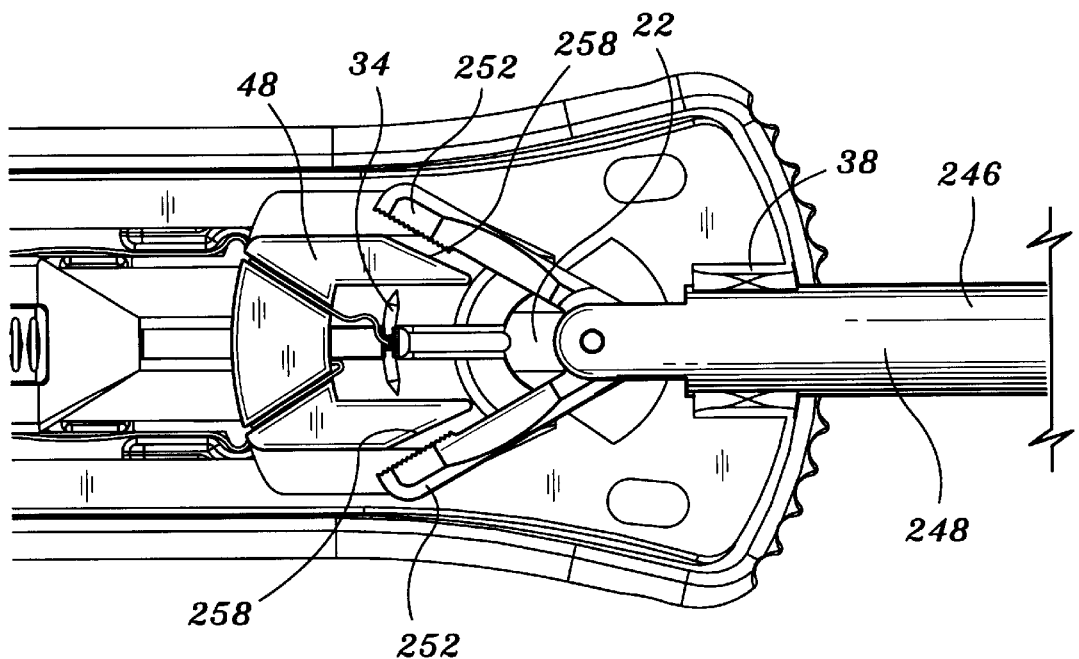
FIG. 35 is an enlarged top view of the body portion showing the suturing apparatus of FIG. 33 mounted in the loading unit thereon.

Referring to FIG. 35, suturing apparatus 246 is mounted in U-channel 38 in an open position. U-channel 38 is dimensioned and configured to receive tubular member 248 and releasably secure tubular member 248 therein. Needle dispensing portion 48 of loading unit 22 has angled ends 258 which are substantially parallel to jaw elements 252 in the open position when suturing apparatus is mounted onto loading unit 22. Upon mounting suturing apparatus 246, first suture needle 34 has ends in alignment with recesses 254 (FIG. 34) of jaw elements 252.

Figure 36:
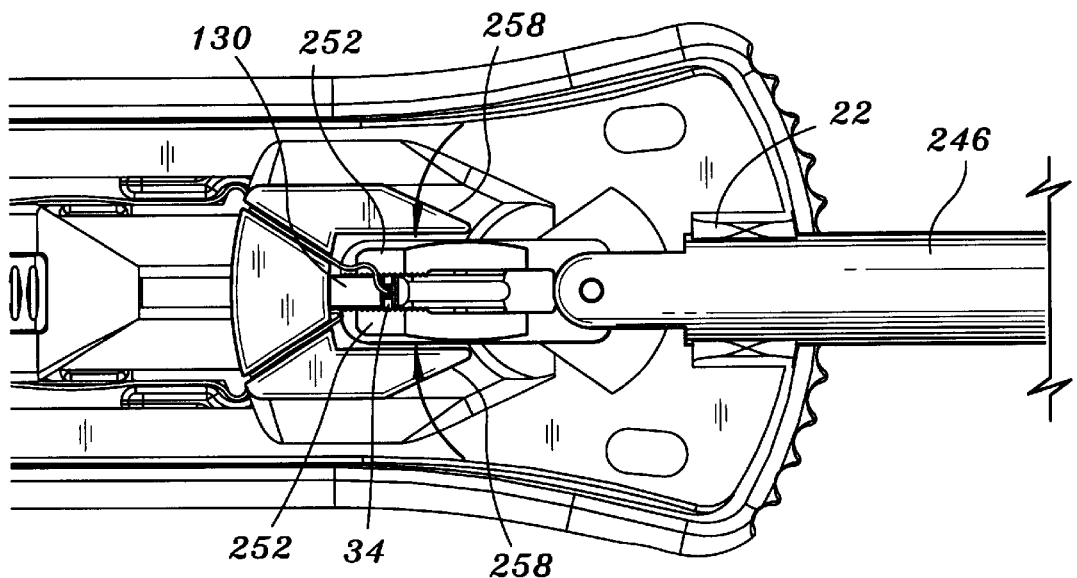
FIG. 36 is an enlarged top view of the body portion showing the suturing apparatus of FIG. 33 having jaw elements in a closed position.

Referring to FIG. 36, angled ends 258 act as a safety mechanism and permit loading of suturing apparatus 246 into loading unit 22, however as jaw elements 252 move to a closed position, suturing apparatus 246 cannot be released from loading unit 22 until jaw elements 252 are in a completely closed position. Recess 254 (FIG. 34) of each jaw element 252 is aligned with first suture needle 34 disposed in needle tray 130 when suturing apparatus 246 is loaded within loading unit 22. Jaw elements 252 are closed onto first suture needle 34 and received in recesses 254 (FIG. 34).

Figure 37:
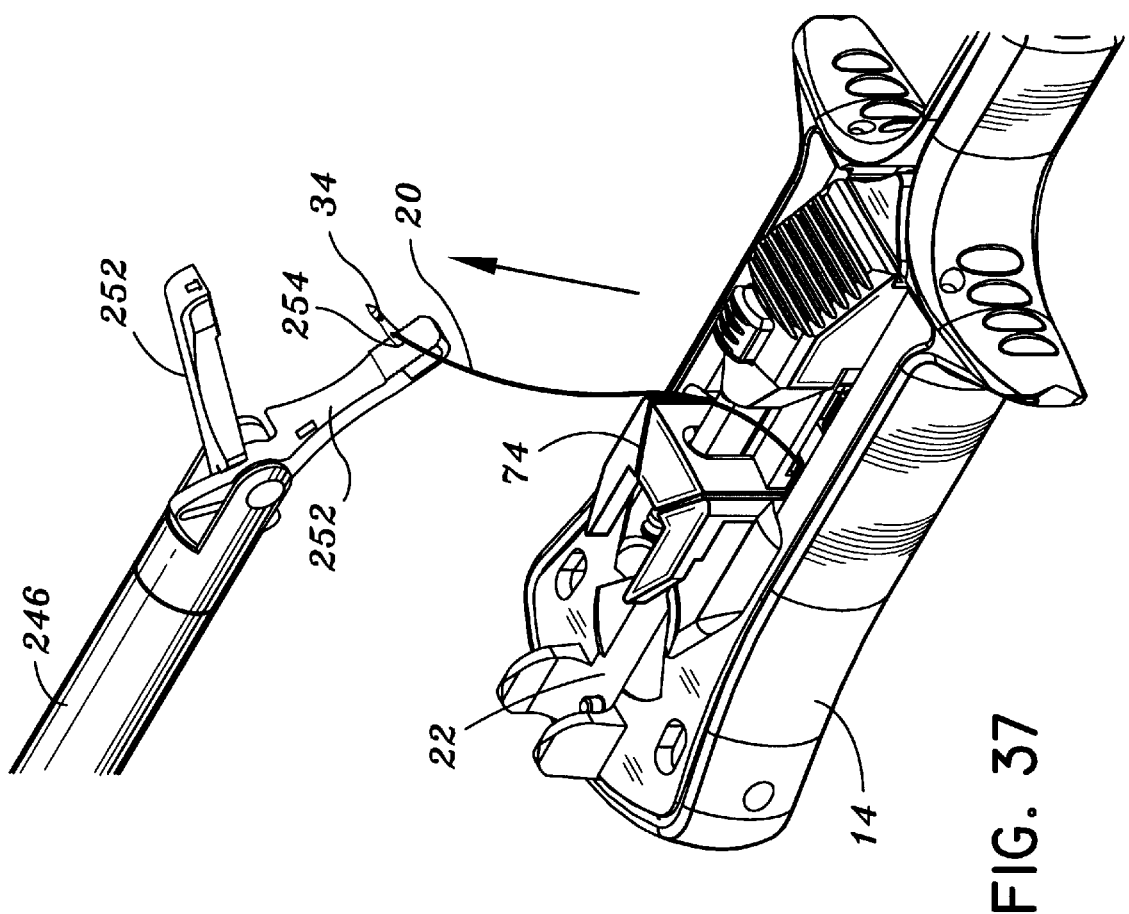
FIG. 37 is a perspective view of the suturing apparatus dismounted from the loading unit.

Referring to FIG. 37, suturing apparatus 246 is removed from loading unit 22 by first opening jaw elements 252. Suture 20 is removed from suture guides 74, and jaw elements 252 remain opened. First suture needle 34 is secured in one jaw 252 by securing blades 256 (FIG. 38), and suturing apparatus 246 is ready for suturing tissue.

Figure 38:
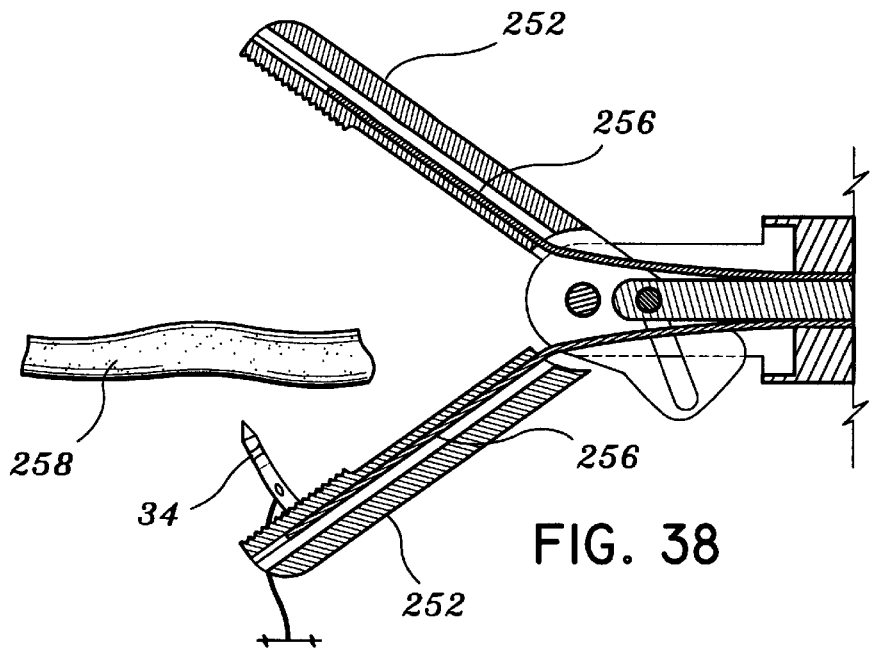
FIG. 38 is a side cross-sectional view of the suturing apparatus prior to applying a suture to soft tissue.
Figure 39:
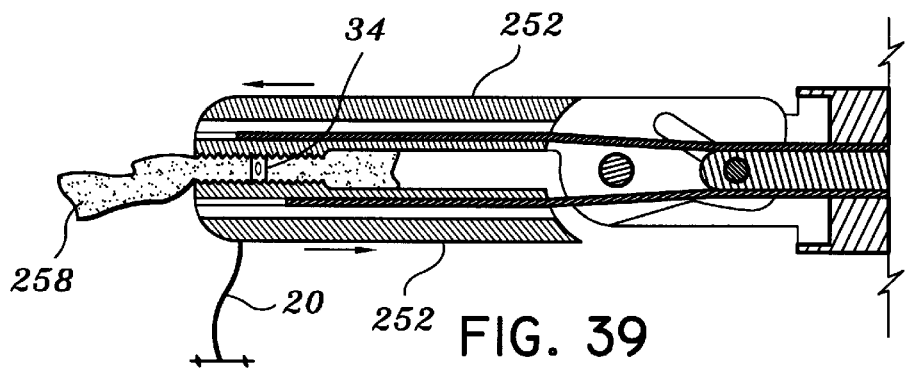
FIG. 39 is a side cross-sectional view of the suturing apparatus with the suture needle penetrating soft tissue.
Figure 40:
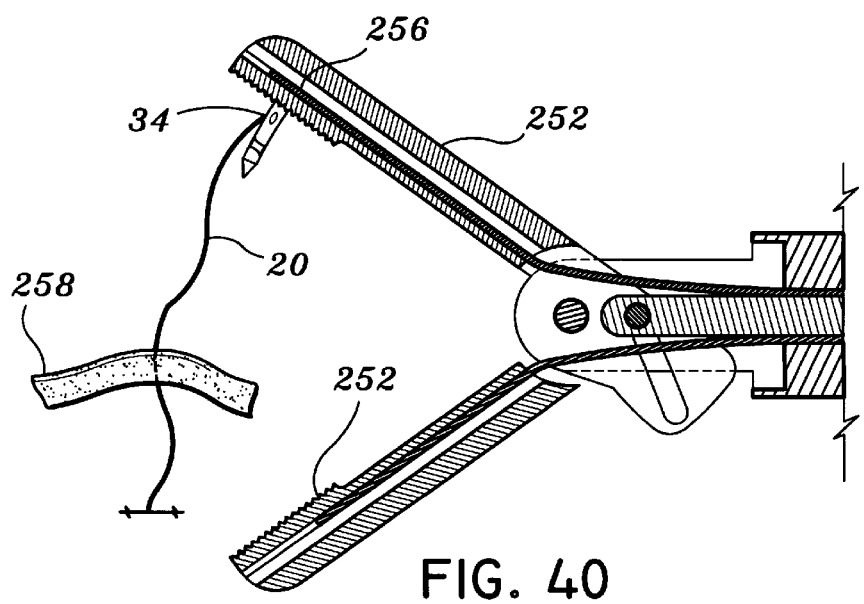
FIG. 40 is a side cross-sectional view of the suturing apparatus drawing the suture through soft tissue.

Referring to FIGS. 38–40, jaw elements 252 are in the open position prior to application of suture 20 (FIG. 38). Securing blade 256 secures first suture needle 34 in jaw element 252. Jaw elements 252 are closed on soft tissue 258. First suture needle 34 penetrates through soft tissue 258 and is received within the opposing jaw element 252 (FIG. 39). Jaw elements 252 are opened, securing blade 256 locks first suture needle 34 in the opposing jaw element 252, and suture 20 is pulled through soft tissue 258. Suturing is continued to secure soft tissue 258 to bone 238, or alternately secure a prosthetic device to bone.

Referring to FIGS. 41 and 42, when suturing with first suture needle 34 is complete, first suture needle 34 is removed from recess 254 in jaw elements 252 (FIG. 37). Suturing apparatus 246 is now ready to be reloaded with second suture needle 72. Button 144 is depressed moving rod 148 down and releasing extensions 154 from first recess portion 176a of slot 128. Slide 24 and needle tray 130 may be proximally translated to the second recess portion 176b corresponding to second position. Button 144 is released to lock slide 24 and needle tray 130 in second position. Movement of needle tray 130 locates second suture needle 72 in communication with recesses 254 of jaw elements 252 (FIG. 37) such that second suture needle 72 can be loaded when suturing apparatus 246 is loaded in loading unit 22 (FIG. 37). Needle tray 130 preferably drops down when presenting second suture needle 72 for loading. Suturing may now be performed with second suture needle 72 as described for FIGS. 38–40 above.

Figures 43, 44:
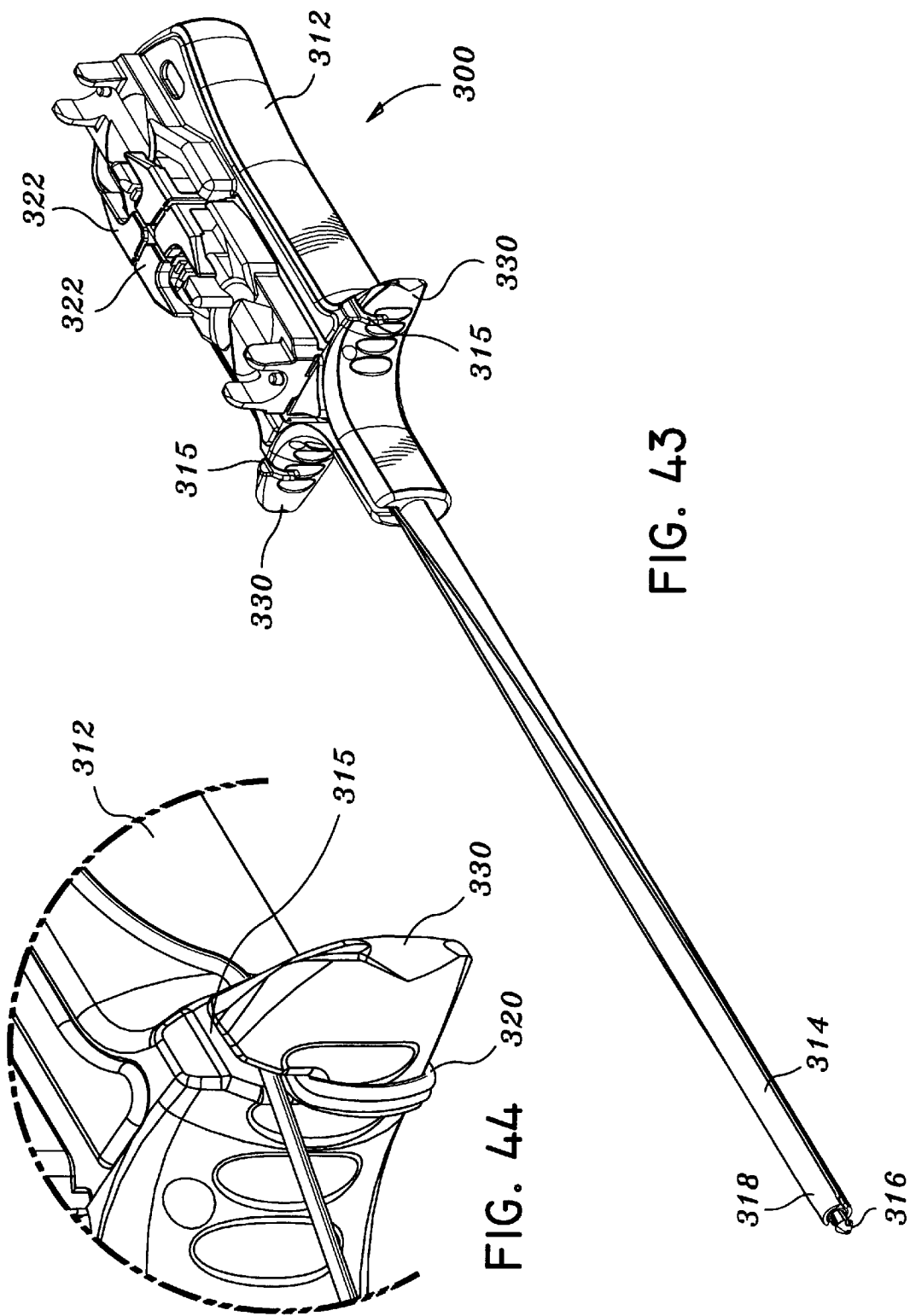
FIG. 43 is a perspective view of another suture anchor installation system.
FIG. 44 is a magnified view showing slots in a body portion of the suture anchor installation system of FIG. 43.

Referring to FIG. 43, a preferred embodiment of a suture anchor installation system is shown generally as assembly 300. Assembly 300 includes a body portion 312 and an elongated shaft portion 314 extending distally from body portion 312. A suture anchor 316 is shown within a distal end 318 of shaft portion 314. A suture 320 is threaded through suture anchor 316. Suture 320 is routed over shaft portion 314 and into body portion 312. Body portion 314 has loading units 322 disposed thereon and oriented in a bach-to back position as shown in FIG. 43. Body portion 314 further includes slots 315 formed within extensions 330. Further description of each part is described herein.

Referring to FIGS. 43 and 44, extension 330 is shown having suture 320 wrapped thereabout in slot 315. Slots 315 are particularly useful when setting suture anchor 316. As described hereinabove, suture anchor is set within a bone by applying tension to suture 320. With the availability of slots 315, suture 320 is more easily secured to body portion 314 and provides an anchor point to tension suture 320. This feature eliminates the need for wrapping the suture around shaft 314 or a surgeon's hand.

Figure 45:
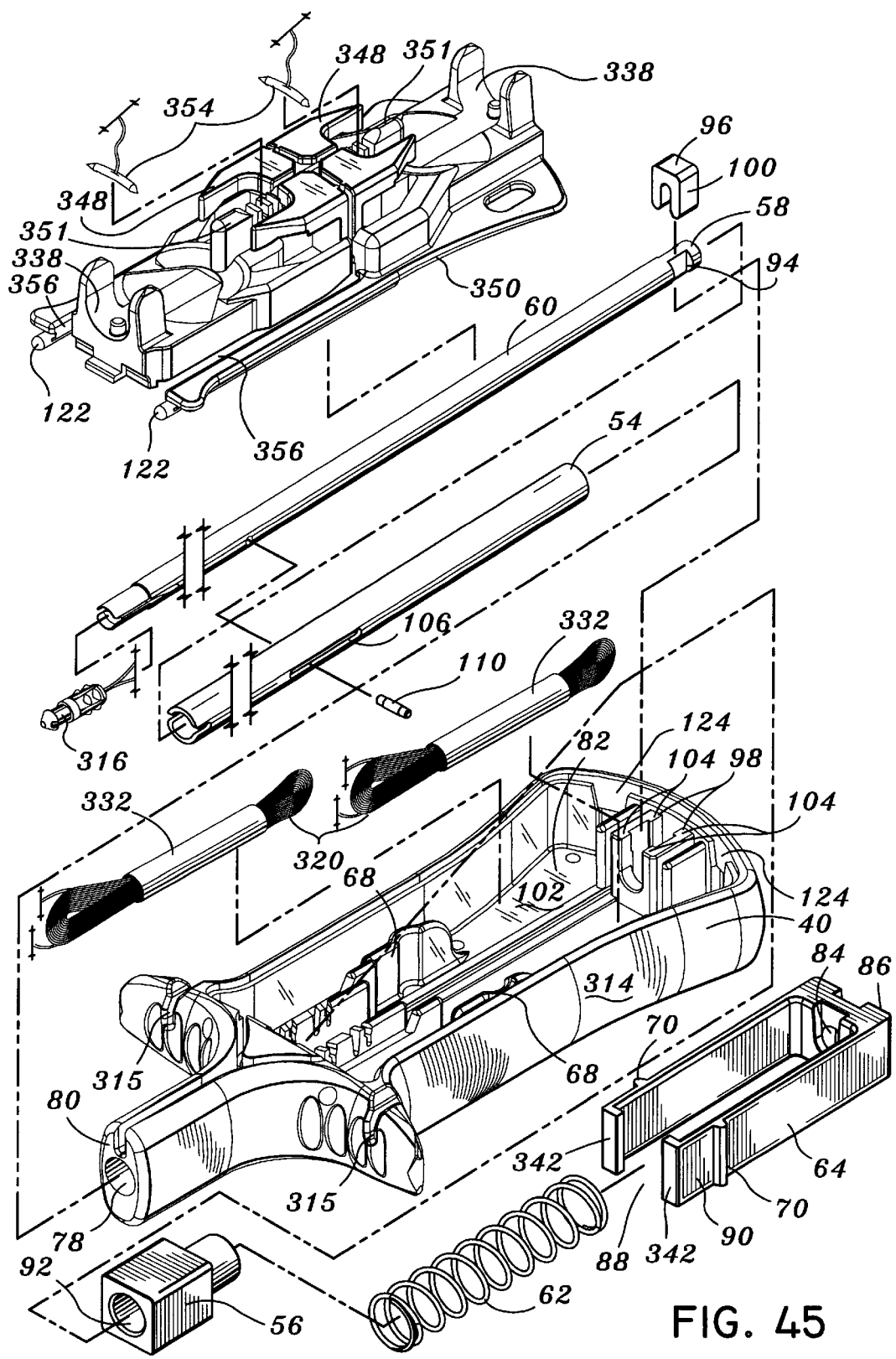
FIG. 45 is a perspective view with parts separated of the suture anchor installation system of FIG. 43.

Referring to FIG. 45, inner shaft 60 is disposed within outer tube 54 when assembled. Body portion 314 defines bore 78 through distal end portion 80. Body portion 314 also defines cavity 82 which is enclosed when a cover 350 is installed. Cavity 82 communicates with bore 78. Inner shaft 60 and outer tube 54 are received in bore 78 and cavity 82. Inner shaft 60 extends through cavity 82 to proximal end portion 40 of body portion 314. Spring housing 64 has bore 84 through proximal end 86 and open portion 88 at distal end 90. Extensions 342 extend inwardly into open portion 88 on spring housing 64. Extensions 342 engage support block 56 while outer tube 54 is distally disposed. Extensions 342 are shown being smaller than extensions 42 of FIG. 6. Extensions 342 are used when a smaller displacement of outer tube 54 is desirable to release suture 320 from tabs 70 and also limit distal travel of outer tube 54 after the implantation of suture anchor 316. Prior to use, tabs 70 and guides grip suture 320 and assist in maintaining suture anchor 316 in a secured position.

Support block 56 also defines bore 92 therethrough. When assembled, inner shaft 60 is disposed within bore 78 of body portion 314, bore 92 of support block 56, spring 62 and bore 84 and opening 86 in spring housing 64.

Flats 94 are formed at proximal end portion 58 of inner shaft 60. C-shaped member 96 is dimensioned and configured to engage flats 94 on interior surfaces 95 of C-shaped member 96 and be received within lateral supports 98 on exterior surfaces 100 of C-shaped member 96. Lateral supports 98 extend from a bottom interior surface 102 at proximal end portion 40 of body portion 314. Lateral supports 98 have extensions 104 extending inwardly. Inner shaft 60 is received between lateral supports 98 and C-shaped member 96 is secured therebetween. C-shaped member 96 prevents rotation and translation of inner shaft 60 by engaging extensions 104 and lateral supports 98.

Outer tube 54 is disposed about inner shaft 60. Outer tube 54 has slot 106 formed longitudinally therein. Inner shaft 60 has hole 108 corresponding to slot 106 which receives pin 110 therethrough. Slot 106 and pin 110 cooperate to limit displacement of outer tube 54 which can translate with respect to inner shaft 60. Outer tube 54 is received through bore 78 of body portion 14 and bore 92 of support block 56. Support block 56 is rigidly attached to outer tube 54. Spring 62 distally biases support block 56 and therefore outer tube 54.

Body portion 314 provides support for suture tubes 332. Prior to deployment of suture 320, suture 320 is stored within suture tubes 332. Suture 320 is arranged in suture tubes 332 such that suture 320 may be drawn from suture tube 332 by pulling on one end of suture 320 in a single direction. Suture 320 is stowed in a looped or "FIG. 8" arrangement. For the best results, loops are stacked on one another to prevent tangles therebetween.

Cover 350 has pins 122 extending distally therefrom for securing cover 350 to body portion 314. Body portion 314 has recesses 124 formed therein for receiving tabs 126 (see FIG. 7). Needle dispenser portions 348 and U-channels 338 of loading units 322 are integrally formed in cover 350 in a back-to-back configuration. Cover 350 has needle trays 351 also integrally formed therein. This embodiment simplifies manufacture and assembly, since cover 350 is a single piece. Further no moving parts are necessary on cover 350 thereby simplifying the method of use.

Figure 46:
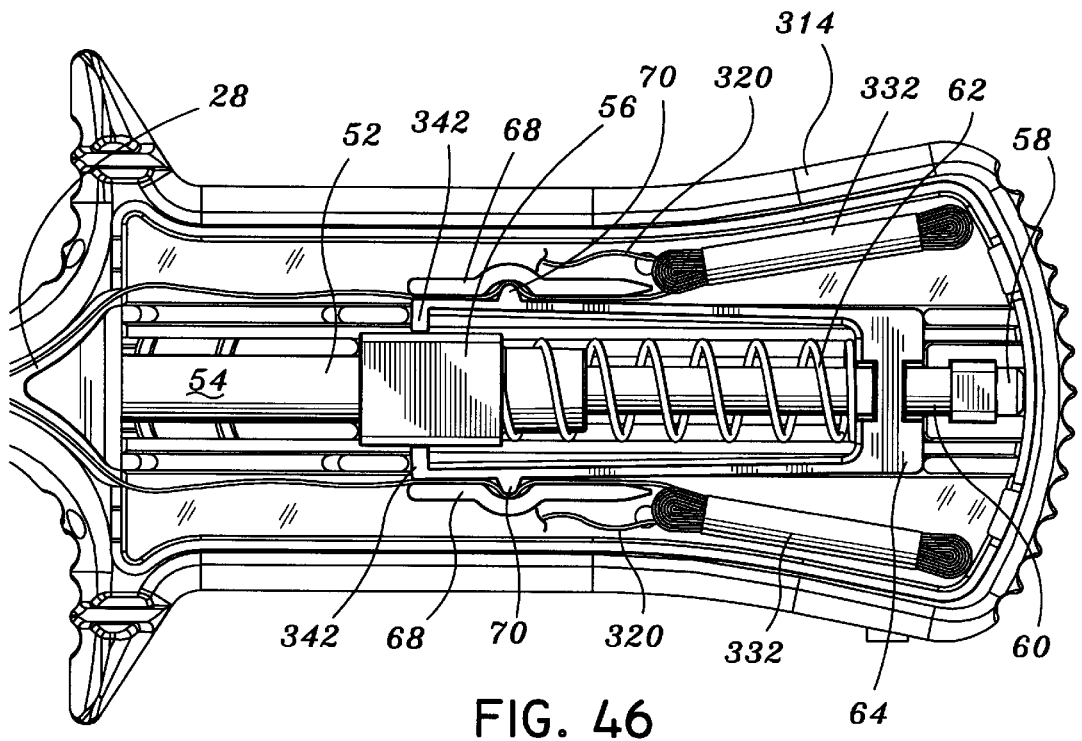
FIG. 46 is an enlarged top view of the body portion of the suture anchor installation system of FIG. 43 with a cover removed.

Referring to FIGS. 46, cover 350 is removed. Proximal end portion 52 of outer tube 54 is shown and received within support block 56. Proximal end portion 58 of inner shaft 60 is disposed within outer tube 54 and rigidly mounted to body portion 314. Outer tube 54 is distally biased by spring 62 disposed within spring housing 64. Spring 62 engages support block 56 and spring housing 64 such that a bias force is applied against outer tube 54 through support block 56. Suture 320 is routed around spring housing 64 and stored within tubes 332 mounted to body portion 314. Exiting suture channel 28, suture 320 is routed between spring housing 64 and guides 68 and secured beneath tabs 70. Extensions 42 engage support block 56 deflecting tabs 70 toward guides 68 and gripping suture 320 therebetween. When support block 56 and therefore outer tube 54 are retracted proximally extensions 342 are released thereby releasing suture 320. Suture 320 further extends to tubes 332 where a portion of suture 320 is stored thereon. Suture 320 extends from tubes 332 and is attached to needles 354 (FIG. 45).

Figure 47:
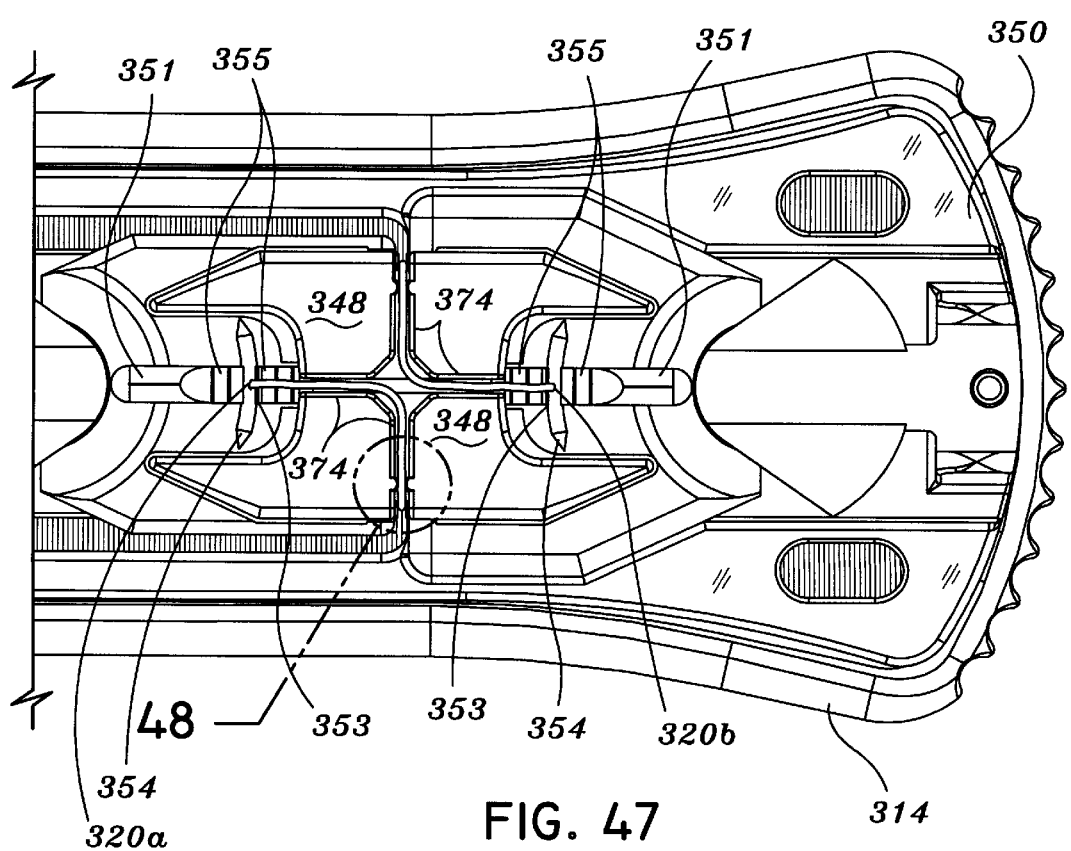
FIG. 47 is an enlarged top view of the body portion of FIG. 46 with the cover replaced.

Referring to FIGS. 46 and 47, cover 350 is shown on body portion 314. Suture 320 extends from tubes 332 over needle dispenser portion 348. Needle dispenser portion 348 includes suture guides 374 formed therein. Suture 320 is a single length of material having two ends 320a and 320b. Ends 320a and 320b attach to needles 354.

Needle trays 351 each have a top portion 352 having a pair of needle notches 353 for receiving and securing needles 354 therein. Relief notches 355 are disposed adjacent to needle notches 353 to provide compliance to needle notches 353 and to allow needles 354 to be inserted and removed therefrom. Cover 350 has slots 356 (FIG. 45) for allowing deployment of suture 320 during a surgical procedure.

Figure 48:
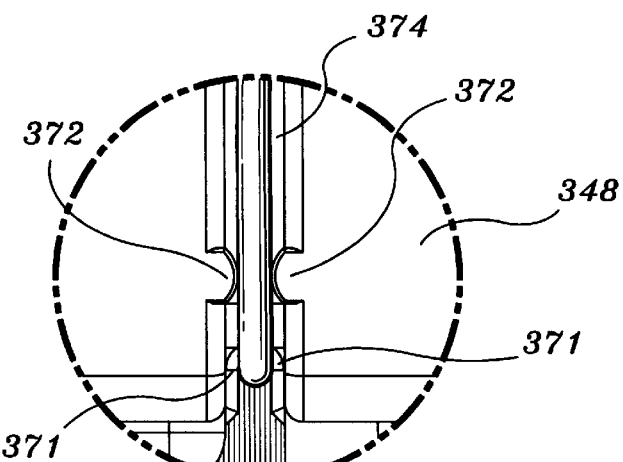
FIG. 48 is a partial top view of the area of detail shown in FIG. 47.

Referring to FIG. 48, suture 320 is routed from tubes 332 (FIG. 46) through suture guides 374. Suture 320 is secured within suture guides 374 by detents 372 and lower detents 371 provided adjacent to suture guides 374. Detents 371 and 372 are dimensioned and configured to releasably secure suture 320 to assist in mounting needles 354 during assembly.

Figure 49:
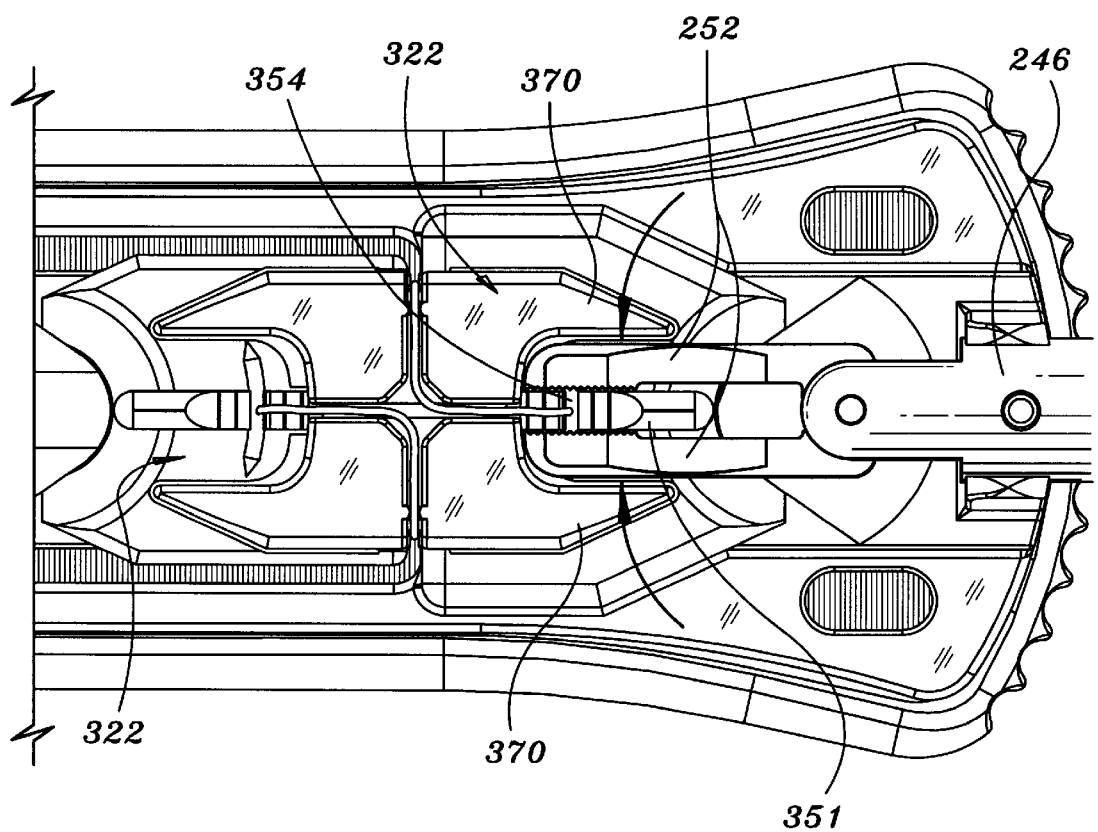
FIG. 49 is an enlarged top view of the body portion of FIG. 43 showing a suturing apparatus in a loading unit.

Referring to FIG. 49, angled ends 370 act as a safety mechanism and permit loading of suturing apparatus 246 into loading unit 322, however as jaw elements 252 move to a closed position, suturing apparatus 246 cannot be released from loading unit 322 until jaw elements 252 are in a completely closed position. Recess 254 (FIG. 34) of each jaw element 252 is aligned with a first suture needle 354 disposed in needle tray 351 when suturing apparatus 246 is loaded within loading unit 322. Jaw elements 252 are closed onto first suture needle 354 and received in recesses 254 (FIG. 34). Suturing is then performed as described above. After first needle 354 is disengaged from suturing apparatus 246, a second suture needle 354 from the remaining loading 322 may be loaded into suturing apparatus 246 following the same method as described above.

Figure 50:
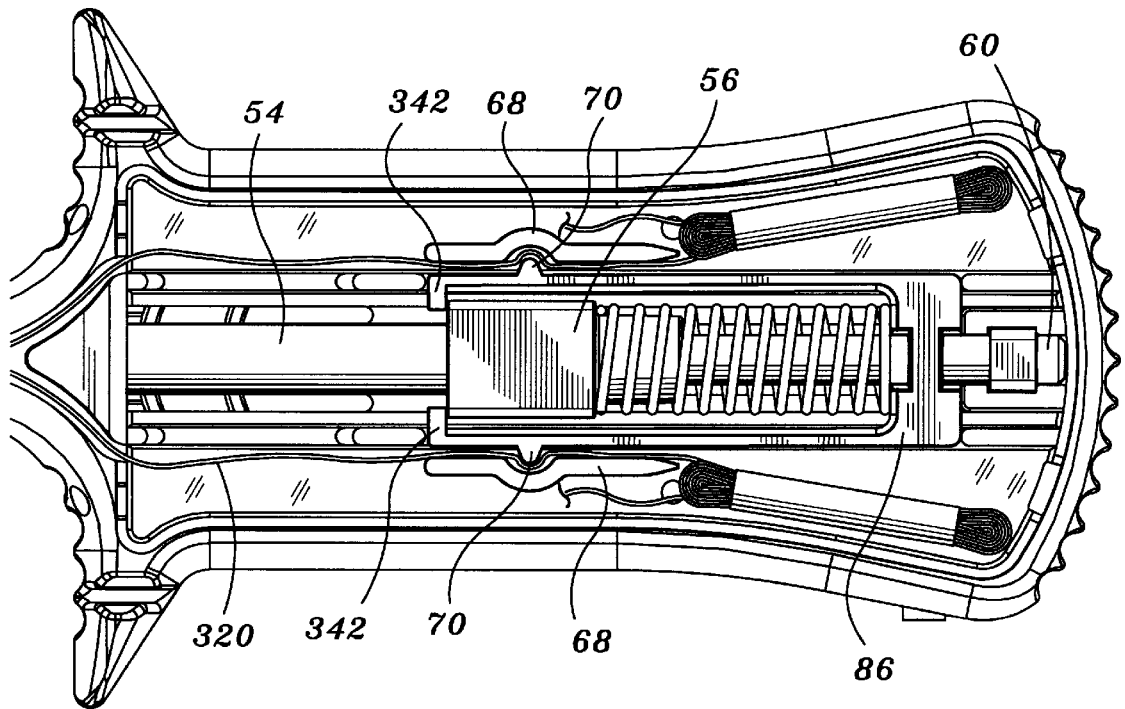
FIG. 50 is an enlarged top view of the body portion of the suture anchor installation system of FIG. 43 with a cover removed and a support block retracted.
Figure 51:
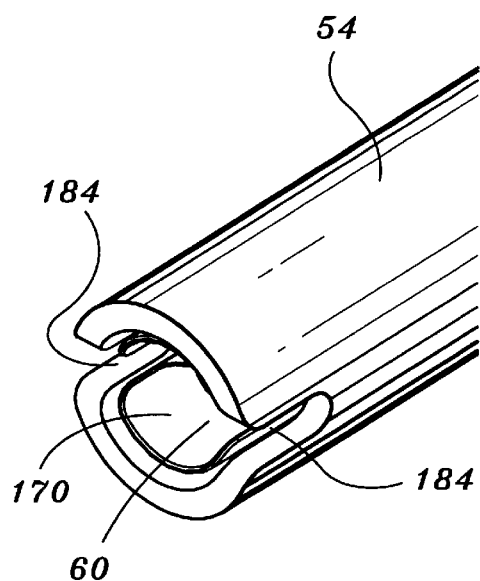
FIG. 51 is a perspective view of a distal end portion of the suture anchor installation system of FIG. 43.

Referring to FIGS. 50 and 51, when a predetermined depth within a bone is reached by suture anchor 316 (FIG. 43), support block 56 which is rigidly attached to outer tube 54 moves proximally beyond extensions 342 in spring housing 86. Extensions 342 move inwardly retaining support block 56 and outer tube 54 in a proximally retracted position. This position releases suture 320 from the stowed position in grooves 184 at distal end portion 170 of inner shaft 60. Extensions 342 are reduced in size from extensions 42 of FIG. 28. In this way, a shorter stroke of outer tube 54 will release suture 320 from between tabs 70 and guides 68. Another advantage of this configuration includes allowing the distal end of inner shaft 60 to be protected after implanting suture anchor 316 since outer tube 54 will overlap the distal end of inner shaft 60.

It will be understood that various modifications may be made to the embodiments disclosed herein. For example, needle trays can support multiple suture needles. Therefore, the above description should not be construed as limiting, but merely as exemplifications of preferred embodiments. Those skilled in the art will envision other modifications within the scope and spirit of the claims appended hereto.

What is claimed is:

1. A suture anchor installation system comprising:

a body portion having a distal end and a proximal end;

an elongated shaft extending distally from the distal end of the body portion, the shaft having a distal end with an annular region disposed thereon for receiving a suture anchor;

a suture retaining member positioned on the body portion, the suture retaining member including tabs for gripping an at least one suture;

a loading unit for use with a suturing apparatus mountable on the body portion including a mounting member positioned on the body portion and configured to releasably hold at least one suture needle; and the loading unit further including a receiving structure formed in the body portion for receiving a distal end portion of the suturing apparatus in operative alignment with the mounting member to facilitate mounting of the at least one surgical needle in the suturing apparatus.

2. A suture anchor installation system as recited in claim 1 further comprising a suture anchor attachable within the annular region and comprising a setting portion and an engagement portion, the suture anchor having at least one suture associated therewith and the at least one suture extending from the suture anchor to maintain the setting portion within the engagement portion of the suture anchor.

3. A suture anchor installation system as recited in claim 2 wherein the at least one suture needle is associated with the at least one suture extending from the suture anchor.

4. A suture anchor installation system as recited in claim 1 further comprising a slide attaching to the mounting member for repositionably mounting the mounting member on the body portion for positioning suture needles to facilitate mounting of the suture needles in the suturing apparatus.

5. A suture anchor installation system as recited in claim 1 wherein the body portion defines a cavity therein for storage of the at least one suture.

6. A suture anchor installation system as recited in claim 5 further comprising a cover for enclosing at least a portion of the cavity, the loading unit being integrally disposed on the cover.

7. A suture anchor installation system as recited in claim 5 wherein the at least one suture is stored on spools rotatably disposed within the cavity of the body portion.

8. A suture anchor installation system as recited in claim 5 wherein the at least one suture is stored within tubes disposed within the cavity of the body portion.

9. A suture anchor installation system as recited in claim 1 wherein the mounting member includes a needle tray having a first suture needle and a second suture needle releasably disposed thereon and connected to the at least one suture, the first suture needle and the second suture needle being configured transversely with respect to the needle tray to facilitate mounting of the needles in the suturing apparatus.

10. A suture anchor installation system as recited in claim 9 further comprising a releasable locking mechanism for securing the needle tray in a first loading position corresponding to a first suture needle or a second loading position corresponding to a second suture needle thereby allowing the first suture needle to be loaded by the suturing apparatus when needle tray is locked in the first loading position and the second suture needle to be loaded when the needle tray is locked in the second loading position.

11. A suture anchor installation system as recited in claim 1 further comprises at least two loading units having mounting members wherein the at least two loading units and the mounting members are integrally formed on the body portion.

12. A suture anchor installation system as recited in claim 1 wherein the receiving structure includes a pair of spaced apart alignment tabs forming a U-channel, the tabs guiding an elongate portion of the distal end portion of the suturing apparatus into position on the body portion for loading the at least one suture needle.

13. A suture anchor installation system as recited in claim 1 further comprising a safety mechanism on the loading unit, the safety mechanism preventing the removal of the suturing apparatus for the body portion prior to loading the at least one suture needle.

14. A suture anchor installation system comprising:

a body portion having a distal end and a proximal end;

an elongated shaft extending distally from the distal end of the body portion, the shaft having a distal end with an annular region disposed at the distal end of the shaft, the body portion defining a cavity therein for storage of at least one suture, the at least one suture being stored on spools rotatably disposed within the cavity of the body portion;

a suture anchor attachable within the annular region and comprising a setting portion and an engagement portion, the suture anchor having the at least one suture associated therewith;

an outer tube disposed on the shaft, the outer tube being biased distally and providing support for the suture anchor at a distal end of the outer tube;

a suture retaining member positioned on the body portion, the suture retaining member including tabs to grip the at least one suture extending from the suture anchor to maintain the setting portion within the engagement portion, the tabs being released by inwardly moving extensions releasing grip on the at least one suture by proximally translating the outer tube relative to extensions, the extensions camming against a proximal end portion of the outer tube to release the grip of the tabs;

a loading unit for use with a suturing apparatus mountable on the body portion including a mounting member positioned on the body portion and configured to releasably hold at least one suture needle, the at least one suture needle being associated with the at least one suture extending from the suture anchor;

a slide attaching to the mounting member for repositionably mounting the mounting member on the body portion and for positioning suture needles for loading; and the loading unit including a receiving structure formed in the body portion for receiving a distal end portion of the suturing apparatus in operative alignment with mounting member to facilitate mounting of the at least one surgical needle in the suturing apparatus.

15. A suture anchor installation system as recited in claim 14 further comprising a cover for enclosing at least a portion of the cavity, the loading unit being integrally disposed on the cover.

16. A suture anchor installation system as recited in claim 14 wherein the mounting member includes a needle tray having a first suture needle and second suture needle releasably disposed thereon, the first suture needle and the second suture needle are configured transversely with respect to the needle tray to facilitate mounting of the needles in the suturing apparatus.

17. A suture anchor installation system as recited in claim 16 further comprising a releasable locking mechanism for securing the needle tray in a first loading position corresponding to a first suture needle or a second loading position corresponding to a second suture needle thereby allowing the first suture needle to be loaded by the suturing apparatus when the needle tray is locked in the first loading position and the second suture needle to be loaded when the needle tray is locked in the second loading position.

18. A suture anchor installation system as recited in claim 14 wherein the receiving structure includes a pair of spaced apart alignment tabs, the tabs guiding an elongate portion of the distal end portion of the suturing apparatus into position on the body portion for loading the at least one suture needle.

19. A suture anchor installation system as recited in claim 14 further comprising a safety mechanism on the loading unit, the safety mechanism preventing the removal of the suturing apparatus for the body portion prior to loading the at least one suture needle.

20. A suture anchor installation system comprising:
a body portion having a distal end and a proximal end;
an elongated shaft extending distally from the distal end of the body portion, the shaft having a distal end with an annular region disposed thereon for receiving a suture anchor;
a suture retaining member positioned on the body portion, the suture retaining member including tabs for gripping an at least one suture;
a loading unit for use with a suturing apparatus mountable on the body portion including mounting members positioned on the body portion and configured to releasably hold at least one suture needle, the mounting members integrally formed on the body portion; and
the loading unit further including receiving structures formed in the body portion for receiving a distal end portion of the suturing apparatus in operative alignment with the mounting members to facilitate mounting of surgical needles in the suturing apparatus.

21. A suture anchor installation system as recited in claim 20 further comprising a suture anchor attachable within the annular region and comprising a setting portion and an engagement portion, the suture anchor having at least one suture associated therewith and the at least one suture extending from the suture anchor to maintain the setting portion within the engagement portion of the suture anchor.

22. A suture anchor installation system as recited in claim 21 wherein the at least one suture needle is associated with the at least one suture extending from the suture anchor.

23. A suture anchor installation system as recited in claim 20 wherein the body portion defines a cavity therein for storage of the at least one suture.

24. A suture anchor installation system as recited in claim 23 further comprising a cover for enclosing at least a portion of the cavity, the loading unit and mounting members being integrally disposed on the cover.

25. A suture anchor installation system as recited in claim 23 wherein the at least one suture is stored on spools rotatably disposed within the cavity of the body portion.

26. A suture anchor installation system as recited in claim 23 wherein the at least one suture is stored within tubes disposed within the cavity of the body portion.

27. A suture anchor installation system as recited in claim 20 wherein the mounting members include a needle tray having a suture needle releasably disposed thereon and connected to the at least one suture, the suture needle being configured transversely with respect to the needle tray to facilitate mounting of the needles in the suturing apparatus.

28. A suture anchor installation system as recited in claim 27 further comprising two loading units formed on opposite ends of the body portion thereby allowing a first suture needle to be loaded by the suturing apparatus in one loading unit and a second suture needle to be loaded in the other loading unit.

29. A suture anchor installation system as recited in claim 1 wherein the receiving structure includes a pair of spaced apart alignment tabs forming a U-channel, the tabs guiding an elongate portion of the distal end portion of the suturing apparatus into position on the body portion for loading the at least one suture needle.

30. A suture anchor installation system as recited in claim 20 further comprising a safety mechanism on the loading unit, the safety mechanism preventing the removal of the suturing apparatus for the body portion prior to loading the at least one suture needle.

31. A method for applying a suture anchor comprising the steps of:
providing a body portion having a distal end and a proximal end, an elongated shaft extending distally from the distal end of the body portion, the shaft having a distal end with an annular region disposed at the distal end of the shaft, a suture anchor attachable within the annular region and comprising a setting portion and an engagement portion, the suture anchor having at least one suture associated therewith, a suture retaining member positioned on the body portion, the suture retaining member including tabs to grip the at least one suture extending from the suture anchor to maintain the setting portion within the engagement portion, a loading unit for use with a suturing apparatus mountable on the body portion including a mounting member positioned on the body portion and configured to releasably hold at least one suture needle, the at least one suture needle being associated with the at least one suture extending from the suture anchor, and the loading unit further including a receiving structure formed in the body portion for receiving a distal end portion of the suturing apparatus in operative alignment with mounting member to facilitate mounting of the at least one surgical needle in the suturing apparatus;
implanting the suture anchor into a bone;
securing the suture anchor within the bone;
mounting the suture apparatus into the receiving structure of the loading unit;
loading the at least one suture needle into the suturing apparatus; and
suturing the suture anchor to soft tissue with the at least one suture needle.

32. A method for applying a suture anchor as recited in claim 31 wherein the step of implanting the suture anchor comprises:
inserting the suture anchor and at least a portion of the annular region into a bore in the bone,
engaging the bone with a distally biased outer tube disposed on the shaft such that the outer tube is retracted proximally when suture anchor and annular portion are advanced distally; and
releasing the at least one suture from the grip of the tabs by camming extensions to release the tabs triggered by the proximal motion of the outer tube.

33. A method for applying a suture anchor as recited in claim 31 wherein the step of securing the suture anchor includes:
drawing the at least one suture proximally; and
camming the setting portion against the engagement portion of the suture anchor to cause the engagement portion to spread and frictionally engage the walls of a bore in the bone.

34. A method for applying a suture anchor as recited in claim 31 wherein the step of loading the at least one suture needle into the suturing apparatus includes:

presenting a first suture needle on a needle tray mounted on the mounting member;

mounting the suturing apparatus onto the receiving structure of the loading unit; and closing jaws at the distal end portion of the suturing apparatus onto the first suture needle to load the first needle for suturing.

35. A method for applying a suture anchor as recited in claim 34 wherein the step of loading the at least one suture needle into the suturing apparatus includes:

presenting a second suture needle on a second needle tray mounted on a second mounting member;

mounting the suturing apparatus onto a second receiving structure of a second loading unit disposed on the body portion; and closing jaws at the distal end portion of the suturing apparatus onto the second suture needle to load the second needle for suturing.

36. A method for applying a suture anchor as recited in claim 31 further comprising the step of:

adjusting a slide to position a second suture needle for loading onto the suturing apparatus.

* * * * *